United States Patent
McKay

(10) Patent No.: US 8,083,722 B2
(45) Date of Patent: Dec. 27, 2011

(54) INSTRUMENTATION FOR INJECTION OF THERAPEUTIC FLUID INTO JOINTS

(75) Inventor: William F. McKay, Memphis, TN (US)

(73) Assignee: Warsaw Orthopedic, Inc, Warsaw, IN (US)

( * ) Notice: Subject to any disclaimer, the term of this patent is extended or adjusted under 35 U.S.C. 154(b) by 105 days.

(21) Appl. No.: 12/605,780

(22) Filed: Oct. 26, 2009

(65) Prior Publication Data

US 2010/0056989 A1    Mar. 4, 2010

Related U.S. Application Data

(63) Continuation-in-part of application No. 12/177,516, filed on Jul. 22, 2008, now abandoned, which is a continuation-in-part of application No. 11/118,125, filed on Apr. 29, 2005, now Pat. No. 7,850,656.

(51) Int. Cl.
 *A61M 5/00* (2006.01)
(52) U.S. Cl. .......... 604/173; 604/191; 604/239
(58) Field of Classification Search .......... 604/173, 604/191, 239, 48
 See application file for complete search history.

(56) References Cited

U.S. PATENT DOCUMENTS

| | | |
|---|---|---|
| 4,013,080 A | 3/1977 | Froning |
| 4,338,925 A | 7/1982 | Miller |
| 4,493,696 A | 1/1985 | Uldall |
| 5,219,358 A | 6/1993 | Bendel et al. |
| 5,354,279 A | 10/1994 | Hofling |
| 5,611,809 A | 3/1997 | Marshall et al. |
| 5,628,734 A | 5/1997 | Hatfalvi |
| 5,735,813 A | 4/1998 | Lewis |
| 6,048,346 A | 4/2000 | Reiley et al. |
| 6,077,251 A | 6/2000 | Ting et al. |
| 6,217,554 B1 | 4/2001 | Green |
| 6,241,734 B1 | 6/2001 | Scribner et al. |
| 6,425,887 B1 | 7/2002 | McGuckin et al. |
| 6,972,005 B2 | 12/2005 | Bochm, Jr. et al. |
| 7,094,222 B1 | 8/2006 | Siekas et al. |
| 2001/0016703 A1 | 8/2001 | Wironen et al. |
| 2002/0058947 A1 | 5/2002 | Hochschuler et al. |
| 2002/0099384 A1 | 7/2002 | Scribner et al. |
| 2002/0111603 A1 | 8/2002 | Cheikh |
| 2002/0151867 A1 | 10/2002 | McGuckin, Jr. et al. |

(Continued)

FOREIGN PATENT DOCUMENTS

GB    3555    2/1910

(Continued)

OTHER PUBLICATIONS

International Search Report PCT/2006/014813 mailed Sep. 18, 2006.

(Continued)

*Primary Examiner* — Kevin C Sirmons
*Assistant Examiner* — Imani Hayman

(57) ABSTRACT

Described are novel medical delivery devices that can be used to effectively distribute a medical agent to multiple sites within a tissue volume without requiring the device to be repositioned, including for example to distribute the medical agent within the nucleus pulposus tissue of a spinal disc. Also described are medical delivery devices configured to simultaneously remove fluid from the tissue volume into which a medical agent is being delivered, thus avoiding or otherwise decreasing any pressure build-up and facilitating an effective, uniform delivery of the therapeutic agent.

19 Claims, 19 Drawing Sheets

U.S. PATENT DOCUMENTS

| | | |
|---|---|---|
| 2003/0009132 A1 * | 1/2003 | Schwartz et al. ............ 604/152 |
| 2004/0092894 A1 | 5/2004 | Hung et al. |
| 2004/0215130 A1 | 10/2004 | Rioux et al. |
| 2004/0220536 A1 | 11/2004 | VanTassel et al. |
| 2006/0089567 A1 | 4/2006 | Goldenberg |
| 2006/0276743 A1 * | 12/2006 | MacMahon et al. ............ 604/28 |

FOREIGN PATENT DOCUMENTS

| | | |
|---|---|---|
| WO | WO 00/33909 | 6/2000 |
| WO | WO 02/34113 | 5/2002 |
| WO | WO 2004/030726 | 4/2004 |
| WO | WO 2004/075954 | 9/2004 |

OTHER PUBLICATIONS

Written Opinion PCT/US2006/014813.

* cited by examiner

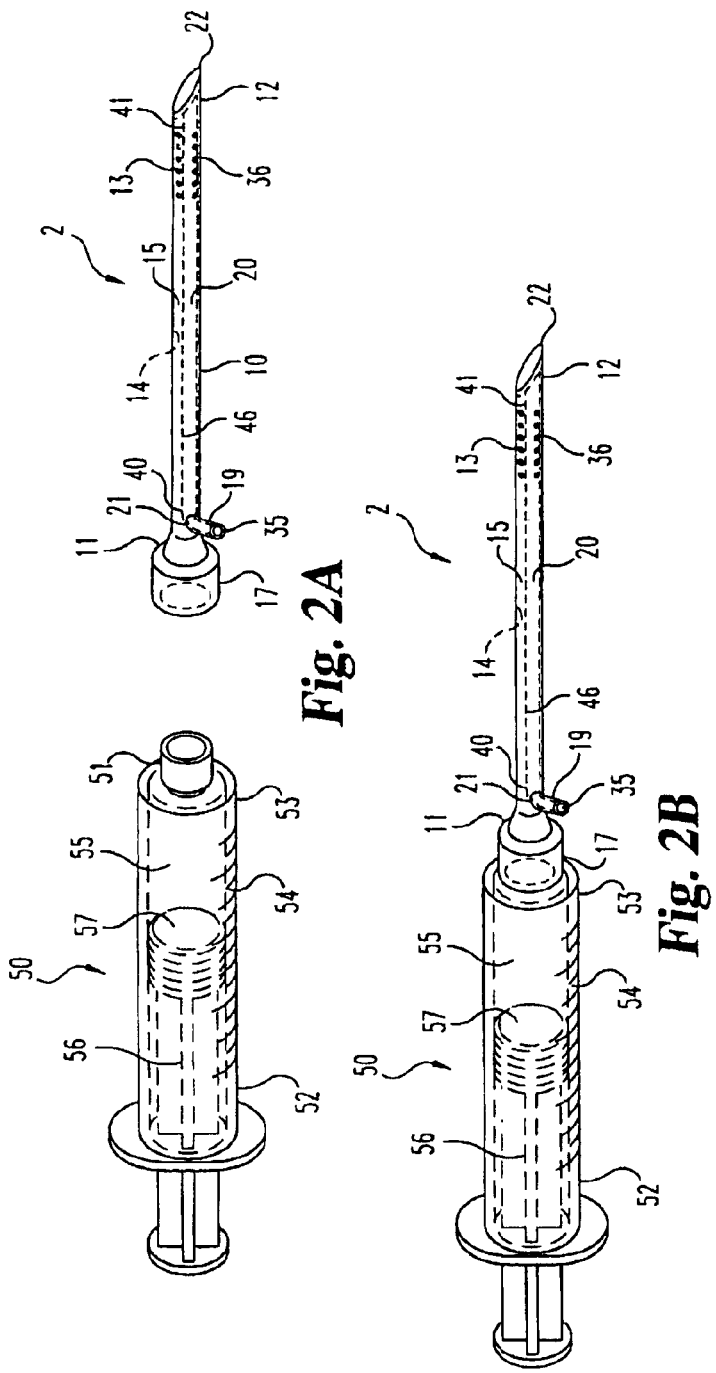
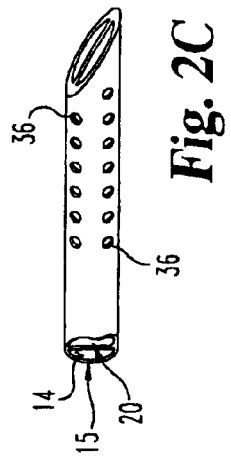

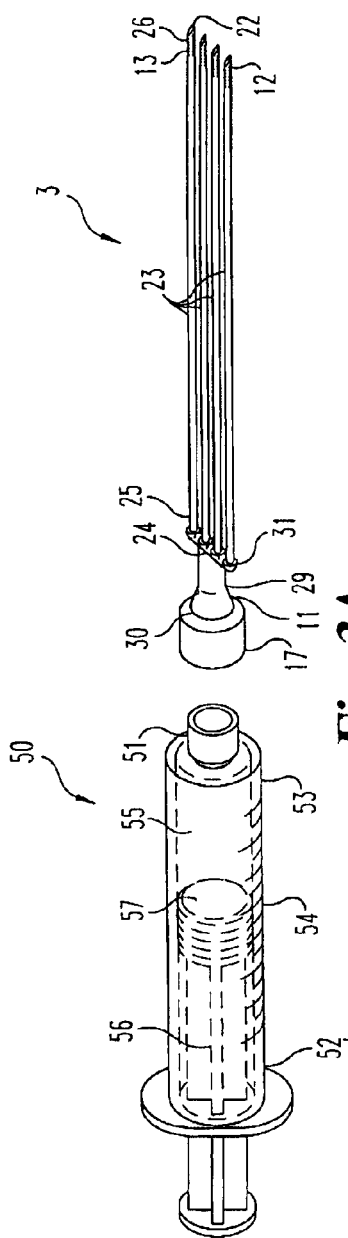
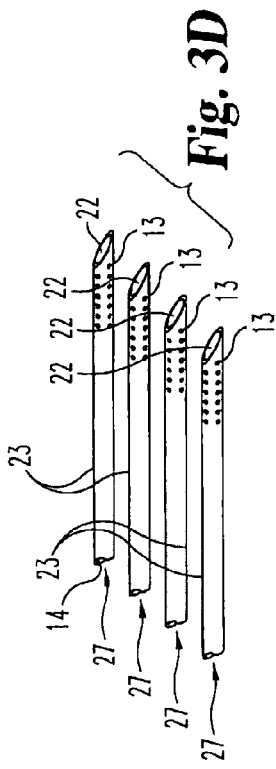
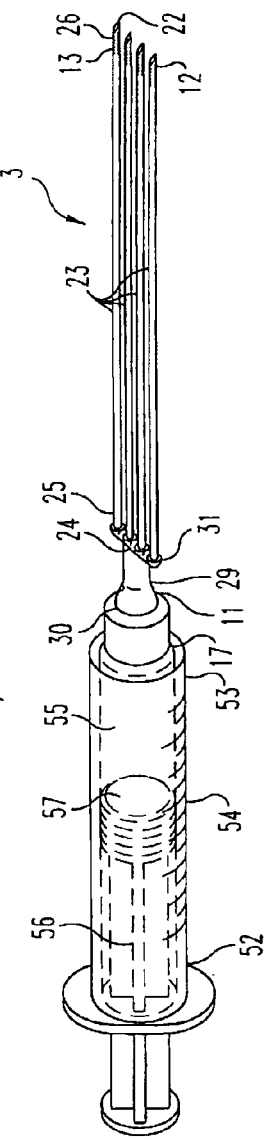
*Fig. 3A*  *Fig. 3B*  *Fig. 3D*

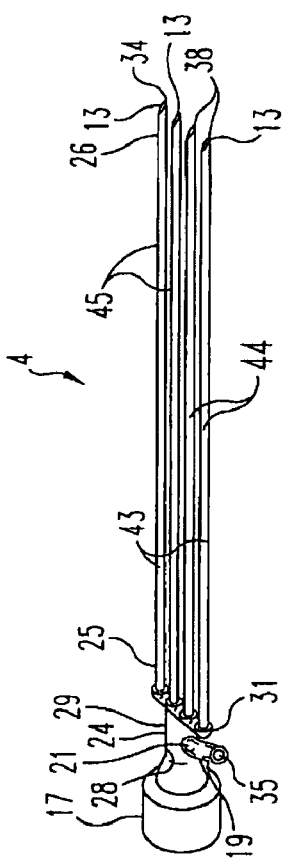
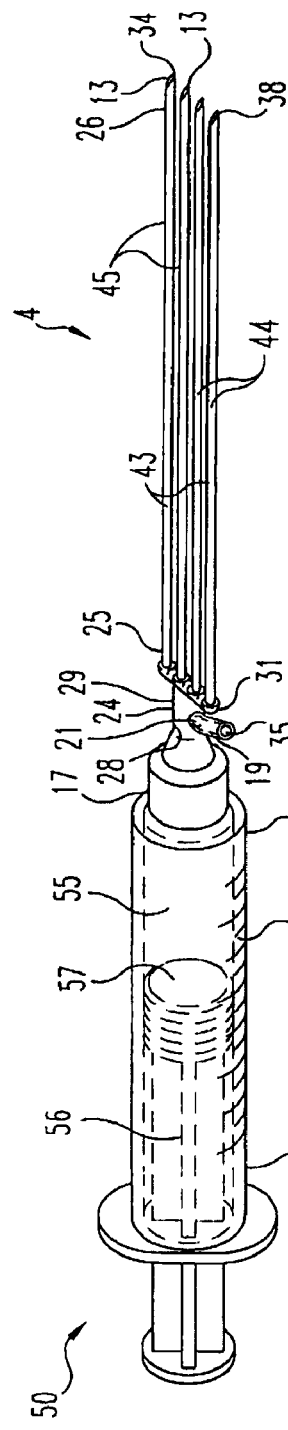
Fig. 4A
Fig. 4C

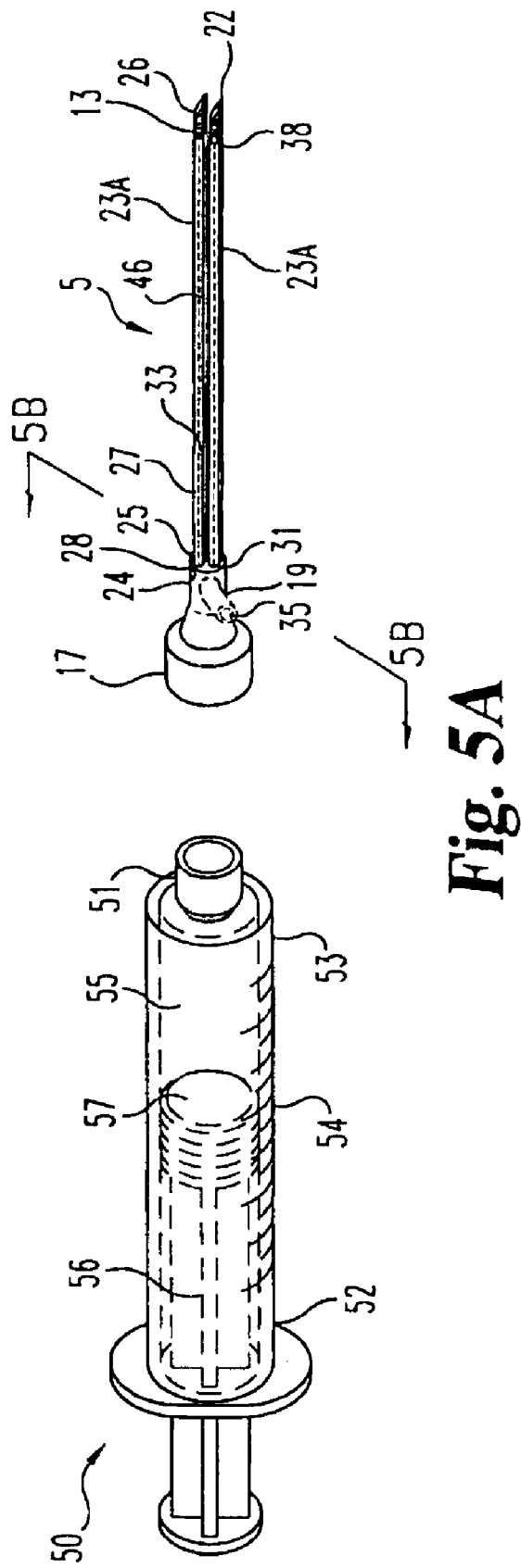

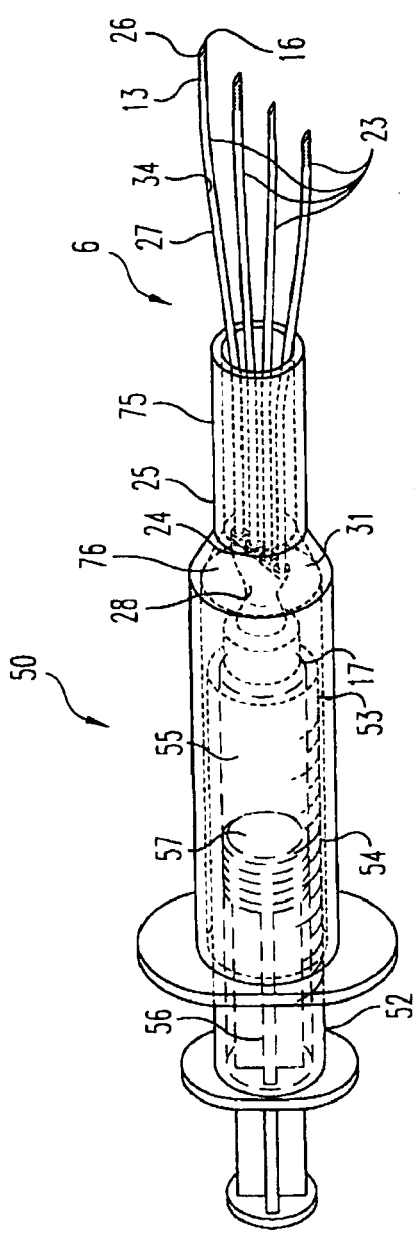

INSTRUMENTATION FOR INJECTION OF THERAPEUTIC FLUID INTO JOINTS

RELATED APPLICATIONS

This application is a continuation-in-part of U.S. application Ser. No. 11/118,125, filed on Apr. 29, 2005. and U.S. application Ser. No. 12/177,516, filed Jul. 22, 2008. The disclosures of both applications are incorporated herein by reference.

FIELD OF THE INVENTION

The present invention relates generally to devices useful for delivering medical agents to patient tissues, and in one particular aspect to medical delivery devices, such as needles, that provide improvements in the diffuse or regional delivery of medical agents through a volume of patient tissue.

BACKGROUND

Many needle devices in current use deliver a single stream of medical agent, and either provide a focused delivery of the agent, or require frequent repositioning to distribute the agent through a volume of tissue. Repeated positioning of a device can cause discomfort to the patient and can lead to extended tissue damage. Additionally, current devices and methods for delivering medical agents can cause localized pressure as the agent is delivered, making delivery of additional amounts of agent more difficult and potentially causing other patient-related complications.

In view of this background, needs remain for improved or alternative medical agent delivery devices and methods, including for example those that facilitate regional delivery of the agent and/or reduce complications which may arise due to pressure increases in the immediate and/or surrounding tissues. The present invention provides embodiments addressed to these and other needs.

SUMMARY OF INVENTION

The present invention fills the foregoing need by providing methods and systems for injection of large volumes of biological therapeutic fluids into anatomical spaces.

The present invention provides medical delivery devices, such as needles, that can be used to effectively distribute a medical agent to multiple sites within a tissue volume without requiring the device to be repositioned, including for example to distribute the medical agent within the nucleus pulposus tissue of a spinal disc. In certain embodiments, medical delivery devices of the invention are also configured to simultaneously remove fluid from the tissue volume into which a medical agent is being delivered, thus avoiding or otherwise decreasing any pressure build-up and facilitating an effective, uniform delivery of the therapeutic agent.

In specific embodiments, methods and devices are adapted for medical agent delivery into nucleus pulposus tissue of a spinal disc. Such deliveries in accordance with the invention provide particular advantage in many respects, since the nuclear tissue of the disc is substantially non-vascularized and thus the native capacity for distribution of the medical agent is limited. As well, in instances where the disc annulus remains substantially intact or has a relatively small opening, a relatively closed volume exists into which the agent is to be delivered thus increasing the potential for pressure build within the disc space and/or undesired expulsion of delivered and/or tissue material back out of the opening.

In one aspect, needles for delivering a therapeutic fluid to a target space are provided. Such needles comprise one or more elongated tissue-penetrating members for penetrating into a target space, at least one extraction orifice located on said one or more tissue-penetrating members, an extraction fluid path in fluid communication with said at least one extraction orifice, at least one injection orifice located on said one or more tissue-penetrating members and positioned remotely from said at least one extraction orifice, and an injection fluid path in fluid communication with said at least one injection orifice.

The number of extraction and injection orifices, their size, and their position relative to each other are selected to create a pressure gradient within the target space when a therapeutic fluid is injected through the at least one injection orifice. The location of the extraction and injection orifices relative to each other depends on the type of target space being treated, and more specifically, on the content and type of target space content, such as target space fluids or target space tissue.

The lumens of the needle may be in a concentric relation or may be adjacent to each other. When the lumens are adjacent to each other, preferably the orifices are formed in the sidewalls of the lumen. Such orifices may be referred herein as sidewall orifices. In one specific embodiment, a sidewall extraction orifice may comprise a series of holes with progressively increasing diameter towards the proximal end of the needle, while a sidewall injection orifice may comprise a series of holes with progressively increasing diameter towards the distal end of the needle. When the lumens are in a concentric relationship, the outside lumen may have a sidewall orifice and the inside lumen may have a orifice at the distal end, with outside lumen, preferably, serving as an extraction lumen.

The instant needle may be connected to an infusion device such as a infusion device, a catheter, or a pump. Such device may comprise extraction and injection chambers that are fluidly isolated from each other. The extraction chamber and the injection chamber are in fluid communication with the extraction lumen and the injection lumen of the needle respectively. Alternatively, independent infusion devices may be connected to each lumen of the instant needle.

In a preferred embodiment, the infusion device comprises a multi-chamber infusion device. Such infusion device may include an extraction plunger slidably disposed in the extraction chamber and an injection plunger slidably disposed in the injection chamber. The plungers can be activated independently of each other to create a positive or negative pressure within their respective chambers.

In another aspect, a method of delivering therapeutic fluid to a target space is provided. The method comprises inserting the instant needle into the target space, creating one or more pressure gradients in the target space, and injecting the therapeutic fluid into the target space. The target space content may be extracted from the target space through the one or more extraction orifices by activating the extraction plunger to create a negative pressure within the extraction chamber. Concurrently or sequentially, the therapeutic fluid may be injected into the target space through the one or more injection orifices by activating the injection plunger to create a positive pressure within the infusion chamber. Preferably, the fluids are exchanged in equal amounts.

BRIEF DESCRIPTION OF THE FIGURES

FIG. 2A is an exploded view of an embodiment of an alternative syringe needle assembly provided according to the present invention.

FIG. 2B is a side elevation view of the syringe needle assembly of FIG. 2A.

FIG. 2C is an exploded view of distal region of the syringe needle assembly of FIG. 2A.

FIG. 3A is an exploded view of an embodiment of an alternative syringe needle assembly having a manifold and a plurality of needles.

FIG. 3B is a side elevation view of the syringe needle assembly of FIG. 3A.

FIG. 3D is fragmentary view depicting the distal tip region of the needle assembly shown in FIG. 3A.

FIG. 4A is an exploded view of an embodiment of an alternative syringe needle assembly having elongated needle members devoted to fluid delivery and withdrawal.

FIG. 4C is a side elevation view of the syringe needle assembly of FIG. 4A.

FIG. 5A is an exploded view of an alternative syringe needle assembly having a manifold and having elongated members devoted to fluid delivery and withdrawal.

FIG. 6 is a side elevation view of an embodiment of a syringe needle assembly having the distal ends of the elongated members partially expelled from a retaining sleeve having a single internal lumen.

FIG. 7 is a side elevation view of the syringe needle assembly of FIG. 1 in use to deliver a medical agent into an interior spinal disc space.

FIG. 15b shows a cross-section area of the needle embodiment presented in FIG. 15a.

FIG. 16b shows a cross-section area of the needle embodiment presented in FIG. 16a.

DETAILED DESCRIPTION

Figure 1A:
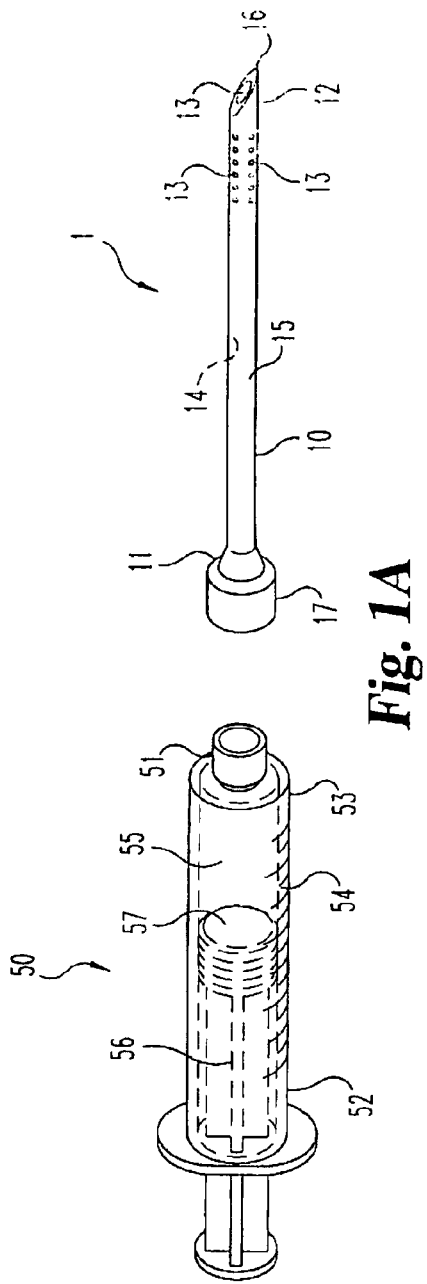
FIG. 1A is an exploded view of one embodiment of a syringe needle assembly according to the present invention.

For purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

As disclosed above, the present invention provides methods, medical devices, and components of medical devices useful for delivering one or more medical agents into patient tissues, including in certain specific embodiments into the nucleus of a spinal disc. Certain methods and devices of the invention desirably achieve a regional, rather than single pinpoint, delivery of the medical agent. In alternative forms, methods and devices of the invention capitalize upon the removal of fluid and/or other volume-occupying tissue material to minimize or eliminate pressure buildup upon the delivery of medical substances into the tissue region.

Figure 1B:
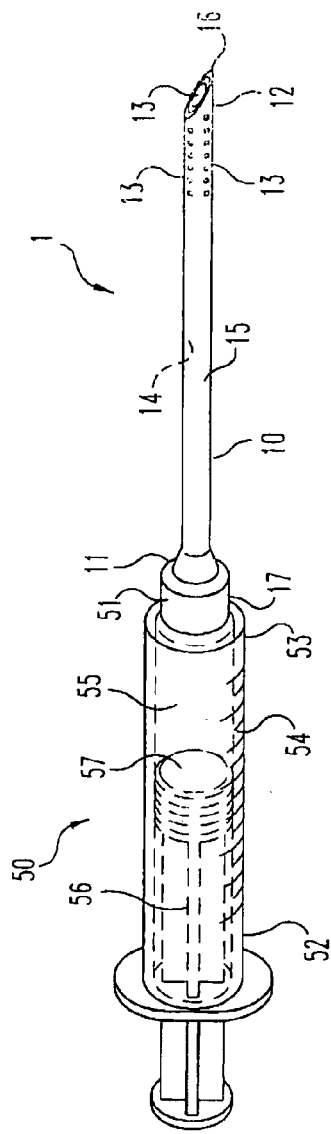
FIG. 1B is a side elevation view of the syringe needle assembly of FIG. 1A.
Figure 1C:
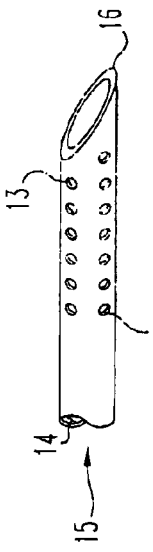
FIG. 1C is an exploded view of distal region of the syringe needle assembly of FIG. 1A.

With reference now to FIGS. 1A, 1B and 1C, shown is one embodiment of a medical delivery device of the invention that generally includes a needle 1, in certain embodiments a spinal needle configured for penetration through a disc annulus and into nucleus pulposus tissue, and a syringe 50. Needle 1 comprises an elongated member 10 formed of a biocompatible material and has a proximal end 11, a distal region 12, and a plurality of orifices or apertures 13 at its distal region. The elongated member 10 additionally has an inner surface 14 (FIG. 1C) defining a lumen 15 or fluid channel within and along its length. The distal end of elongated member 10 has a penetrating (desirably non-coring) tip 16 to assist penetration into a spinal disc or other patient tissue and ensure the delivery of a medical agent through apertures 13. The proximal end of elongated member 10 has a connector 17 for engaging a distal end of syringe 50. Syringe 50 has a housing 54 having a proximal end 52, a distal end 53 and forming a cavity or internal chamber 55 to provide a supply reservoir for the medical agent. Syringe 50 additionally has a syringe plunger 56 equipped with a plunger head 57 and a connector 51 for attaching to connector 17 of spinal needle 1. With reference particularly to FIG. 1B, the syringe 50 and spinal needle 1 of FIG. 1A are engaged through luerlock connectors 17 and 51 causing cavity 55, lumen 15 and apertures 13 to be in fluid communication. It will be understood, however, that other mechanisms or means for connecting the needle 1 and syringe 50 can be used and are contemplated as being within broader aspects of the present invention.

With reference to FIGS. 2A, 2B and 2C, another medical delivery device of the invention is illustrated that includes a needle 2 and syringe 50. Like needle 1 (FIGS. 1A-1C), spinal needle 2 comprises an elongated tissue-penetrating member formed of a biocompatible material and has a proximal end 11, a distal region 12, and a plurality of orifices or apertures 13 and 36 in the distal region. Orifice 21 and connector 19 are located at the proximal end 11 of elongated member 10. Connector 19 has a lumen 35 and is positioned over orifice 21 causing orifice 21 and lumen 35 to be in communication. The proximal end of elongated member 10 additionally has a connector 17 for engaging a distal end of syringe 50. The elongated member's distal region 12 has a closed penetrating tip 22. Inner member 46, a wall-like structure in contact with the interior surface 14, partitions the interior of elongated member 10 and in combination with inner surface 14, forms first channel 15 and second channel 20 (see e.g. FIG. 2C). Inner member 46 is positioned within elongated member 10 to cause lumen 35, orifice 21, channel 20, and apertures 36 to be in fluid communication and provide a pathway independent of channel 15 for withdrawal of fluid from a spinal disc or other patient tissue. Inner member 46 is similarly positioned to provide for fluid communication between channel 15 and apertures 13. Syringe 50 has a housing 54 having a proximal end 52, a distal end 53 and a cavity or chamber 55. Syringe 50 additionally has a syringe plunger 56 equipped with a plunger head 57 and a connector 51 for attaching to connector 17 of needle 2. With reference particularly to FIG. 2B, the syringe 50 and needle 2 of FIG. 2A are engaged through luer-lock connectors 17 and 51 causing cavity 55, lumen 15 and apertures 13 to be in fluid communication and providing a route for the delivery of a therapeutic agent from syringe 50 through apertures 13. As before, other arrangements for associating the needle and syringe 50 can be used.

Figure 3C:
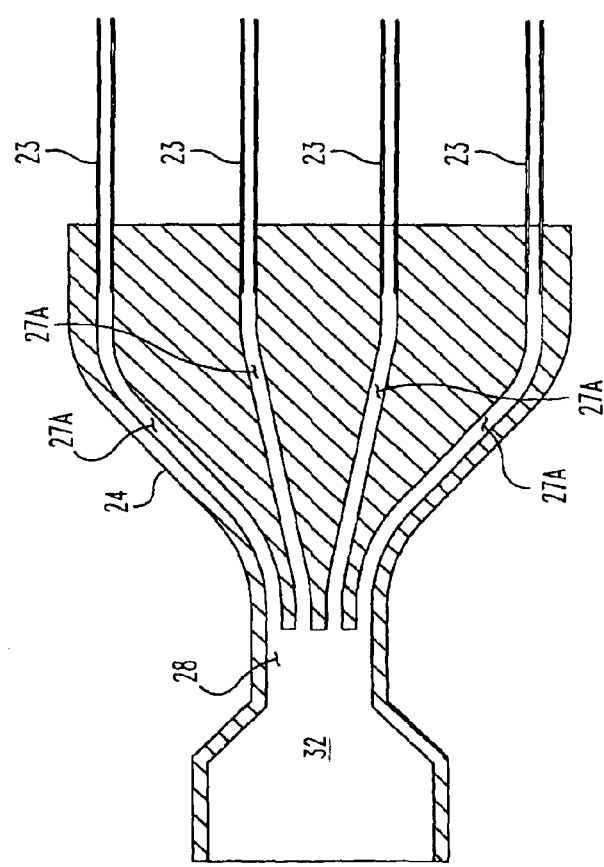
FIG. 3C is a partial cross-sectional view depicting the manifold element and proximal needle region of the syringe needle assembly of FIG. 3A showing internal flow paths.

With reference to FIGS. 3A, 3B and 3C and 3D, another embodiment of a medical device is illustrated that generally includes a needle assembly 3 and a syringe 50. Needle assembly 3 includes a plurality of elongate tissue penetrating members (four needles in the illustrated embodiment) formed of a biocompatible material. In particular, at the proximal end 11, needle assembly 3 has a manifold component 24 and at its distal region 12, a plurality of elongated penetrating members 23 in a generally planar arrangement. Each elongated member 23 has a proximal end 25, a distal region 26 and a plurality of sidewall apertures 13 in its distal region. Elongated members 23 and the manifold piece 24 additionally have inner surfaces 14 and 28 (see e.g. FIG. 3C) defining elongated member lumens 27 and manifold cavity 32. Manifold component 24 also defines a plurality of lumens 27A which receive the proximal ends of elongated members 23 and communicate with their lumens 27. The distal end of elongated member 23 has a closed penetrating tip 22 to assist penetration into a spinal disc upon the application of pressure and allow the delivery of a therapeutic agent through sidewall apertures 13 which in the illustrated embodiment are distributed radially around elongated members 23. The proximal end of manifold piece 24 has a connector 17 for engaging a distal end of syringe 50. Manifold cavity 32 is in fluid communication with lumens 27 and apertures 13. Syringe 50 is as described with regard to FIG. 1. With reference particularly to FIG. 3B, the syringe 50 and spinal needle 3 of FIG. 3A are engaged through luer-lock connectors 17 and 51 causing syringe cavity 55, manifold cavity 32, lumen 27 and apertures 13 to be in fluid communication.

Figure 4B:
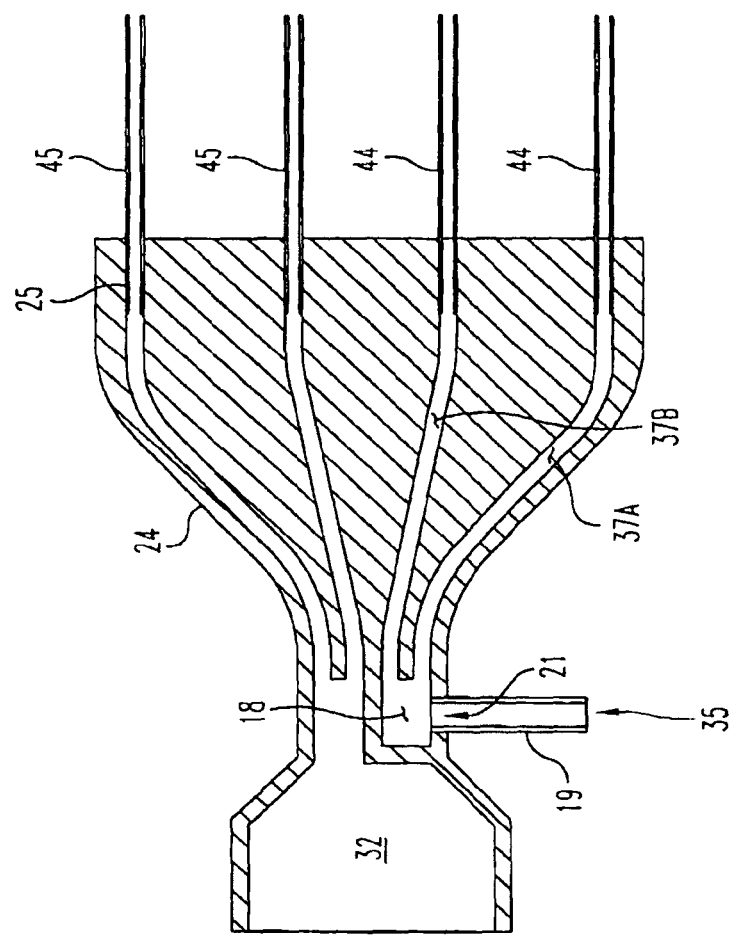
FIG. 4B is a sectional view of the manifold component of the syringe needle assembly of FIG. 4A illustrating separate internal fluid paths for fluid delivery and withdrawal.

With reference to FIGS. 4A, 4B and 4C, another embodiment of an inventive medical delivery device is illustrated that includes a needle assembly 4 and syringe 50. This device is similar to that depicted in FIGS. 3A and 3B, except having separate internal pathways for delivery of medical agent and removal of tissue (e.g. fluid) material. In particular, needle assembly 4 includes a manifold piece 24 and a plurality of elongated tissue penetrating members 44 and 45. Needle assembly 4 has inner walls providing an independent internal pathway 18 for withdrawing or otherwise allowing passage of fluid and/or other material from a spinal disc or other tissue region in conjunction with delivering a therapeutic or other medical agent. Manifold element 24 has a connector 19 positioned on the manifold's outer surface about aperture 21. Connector 19 provides lumen 35 in communication with orifice 21, with channels 37A and 37B of internal pathway 18 and with lumens 42 within elongated members 44 (FIG. 4B).

Elongated members 44 and 45 have a proximal end 25, a distal end 26, a penetrating tip 34 at the distal end 26, and a plurality of apertures 13 and 38. Syringe 50 is as described with regard to FIG. 1. With reference to FIG. 4C, the syringe 50 and needle assembly 4 of FIG. 4A are engaged through luer-lock connectors 17 and 51 causing syringe cavity 55, manifold cavity 32, lumens 43 within delivery members 45 and apertures 13 to be in fluid communication. Thus, plunger 56 can be actuated to deliver medical agent from syringe cavity 55 into manifold cavity 32, through lumens 43 and out of apertures 13. At the same time, tissue fluid or other material can be withdrawn from the tissue volume to receive the medical agent through internal pathway 18 including apertures 38 in elongated members 44, through internal lumens 42, and out through lumen 35. In this regard, the withdrawal of fluid can be active, in the sense that a negative pressure can be applied to pathway 18 through lumen 35 (e.g. using a syringe) to withdraw tissue material, or can be passive in the sense that pressure created in the receiving tissue volume due to the delivery of medical agent can force tissue fluid or other material out through pathway 18.

Figure 5B:
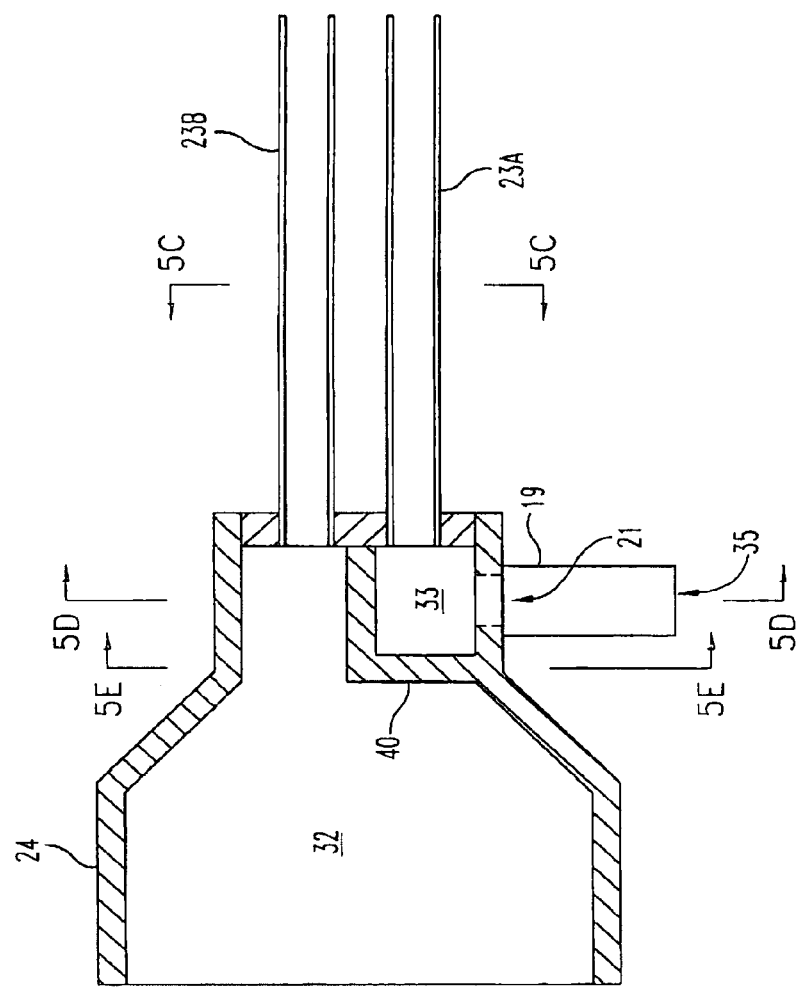
FIG. 5B is a partial sectional view of the needle assembly of FIG. 5A illustrating separate internal fluid paths for fluid delivery and withdrawal.
Figure 5C:
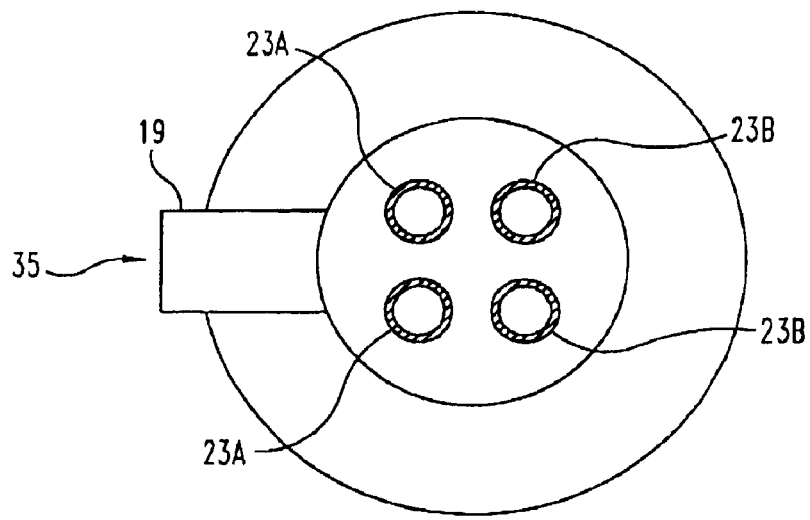
FIG. 5C is a cross-sectional view taken along line 5C-5C of FIG. 5B and viewed in the direction of the arrows.
Figure 5D:
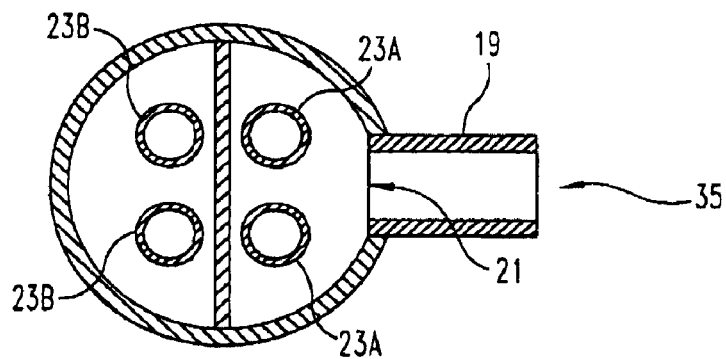
FIG. 5D is a cross-sectional view taken along line 5D-5D of FIG. 5B and viewed in the direction of the arrows.
Figure 5E:
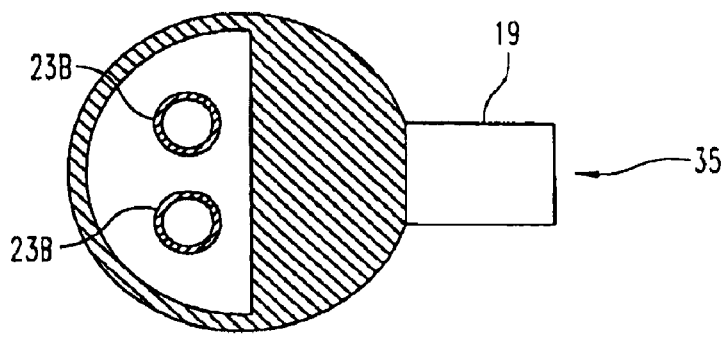
FIG. 5E is a cross-sectional view taken along line 5E-5E of FIG. 5B and viewed in the direction of the arrows.
Figure 5F:
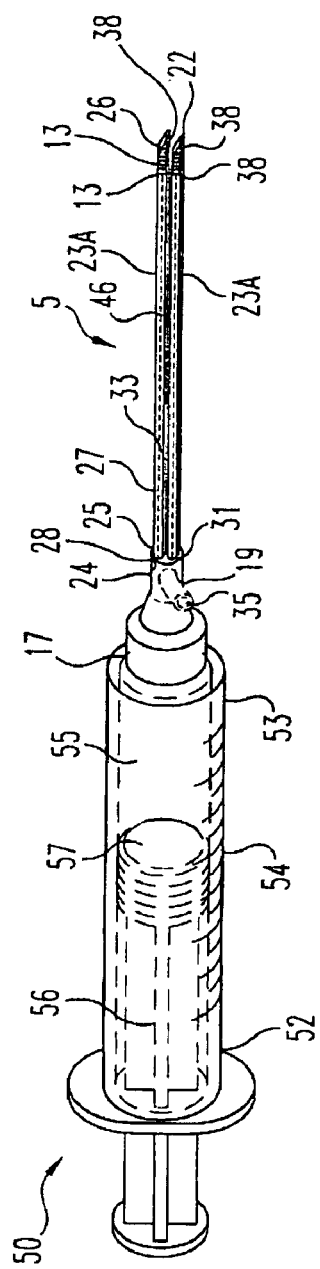
FIG. 5F is a side elevation view of the syringe needle assembly of FIG. 5A.

With reference to FIGS. 5A through 5F, another embodiment of an inventive medical delivery device is illustrated that includes a needle assembly 5 and syringe 50. Needle assembly 5 includes a manifold element 24 and a plurality of elongated tissue penetrating members 23A and 23B constructed from a biocompatible material. Needle assembly 5 is configured to allow for the simultaneous deliver and withdrawal of materials from a spinal disc or other tissue. Withdrawal is achieved through apertures 38 of withdrawing elongated members 23A coupled to withdrawal pathway including channel 33, orifice 21, and lumen 35 of connector 19. The delivery of a medical agent is achieved through apertures 13 of delivery elongated members 23B by way of manifold cavity 32. FIG. 5B is a sectional view of the spinal needle of FIG. 5A illustrating the needle's internal structure. An internal pathway is provided within the elongated members 23A and manifold 24 causing apertures 38, channel 33, orifice 21 and lumen 35 within connector 19 to be in fluid communication. A separate internal pathway is provided causing apertures 13, lumen 27, and manifold cavity 32 to be in fluid communication. With reference to FIG. 5C, a cross-section of the elongated members 23A and 23B taken along line 5C-5C of FIG. 5B and viewed in the direction of the arrows is provided illustrating the position of the elongated members. With reference to FIG. 5D, a cross-section of the proximal end of manifold element 24 taken along line 5D-5D of FIG. 5B is provided illustrating manifold cavity 32 for receiving and transferring medical agent(s) delivered to the patient, and channel 33 for directing material withdrawn from the patient through orifice and lumen 35. With reference to FIG. 5E, a cross section of manifold element 24 at internal wall 40 is provided illustrating the cavity 32 in fluid communication with the connector opening of manifold element 24 for medical agent delivery and internal wall 40 interrupting fluid communication with the connector opening of manifold element 24 and thereby establishing a separate chamber or channel (33, FIG. 5B) for fluid withdrawal. With reference to FIG. 5F, the syringe 50 and needle assembly 5 of FIGS. 5A-5E, are engaged through luer-lock connectors 17 and 51 causing syringe cavity 55, manifold cavity 32, lumens 27 and apertures 13 to be in fluid communication.

Figure 5G:
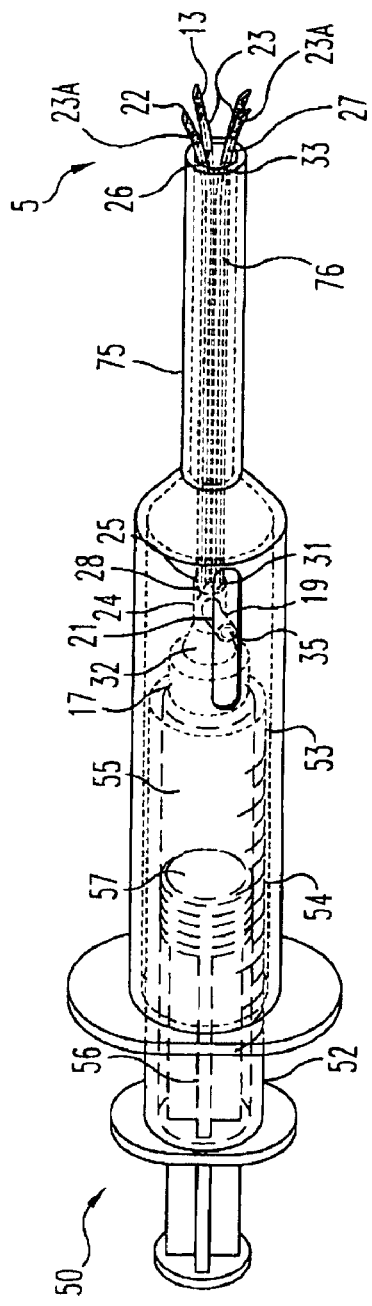
FIG. 5G is a side elevation view of the syringe needle assembly of FIG. 5F in combination with a retaining sleeve with dedicated internal lumens that receive and deflect individual needles to provide a desired injection pattern.

With reference to FIG. 5G, shown is an inventive medical delivery device including the assembly of FIG. 5G engaged with a cannulated retraction sleeve member 75 having a plurality of cannulas 76 having curved end portions to deflect elongated members 23A and 23B to provide a desired injection pattern. In this regard, elongated members 23A and 23B for this embodiment can be constructed of a biocompatible material that is resiliently flexible or deflectable from a relaxed (e.g. straight) configuration, whereby the curved cannulas 76 direct the elongated members to the desired injection pattern when the tips of elongated members 23A and 23B are advanced through and out of the curved cannulas 76, and the elongated members return substantially to their relaxed (e.g. straight) condition when withdrawn back into the cannulas 76 beyond their curved end portions. In other embodiments, the cannulas 76 are straight, and the elongated members have a curved configuration when relaxed but are deflectable to a straight configuration for travel through the cannulas 76. Upon exiting cannulas 76 the elongated members assume their curved configuration to provide the desired delivery pattern. As well, combinations of curved lumens and curved elongated members can be used to achieve a desired delivery pattern. Still further, in alternative embodiments, either some or all of the plurality of elongated members can be of a deflectable nature, and each deflectable elongated member can have a corresponding, dedicated cannula in the cannulated member configured to provide deflection to the desired delivery pattern.

As shown in FIG. 5G, cannulated member 75 can be configured to slide overtop syringe 50 and can include handle or grip elements for facilitating manipulation in proximal and distal directions relative to syringe 50. As well, cannulated member 75 can include windows or cutouts for any syringe components that need or are desired to exit the side of cannulated member 75 (e.g. as in the connector 19 of syringe 50).

With reference to FIG. 6, an embodiment of an inventive medical device is illustrated that includes a needle assembly 6 and syringe 50. Needle assembly 6 is similar in construction to that shown in FIGS. 3A, 3B and 3C, and has elongated penetrating members 23 constructed of flexible biocompatible material having shape memory properties capable of being constrained within sleeve or cannulated member 75 having a single lumen 76 and assuming an original configuration when expelled from lumen 76. In the embodiment shown, the outermost members 23 have curved portions in their unconstrained (relaxed) condition thereby providing a generally wider, planer delivery configuration.

FIG. 7 illustrates the medical delivery device of FIG. 1B in use. In particular, medical agent 85 is being delivered through the plurality of apertures 13 into the nucleus 81 of identified spinal disc 80 to which access has been provided, for example minimally invasive access using the syringe needle assembly potentially in combination with a tubular introducer sleeve.)

Although syringe 50 attached to spinal needle 1 is fitted with a plunger 56 and plunger head 57, a syringe having a screw drive mechanism, a ratcheting mechanism, a trigger, or another delivery mechanism for forcing or otherwise moving the medical agent through the system can be utilized with needle assembly 1 and other needle assembly embodiments of the invention.

Figure 8:
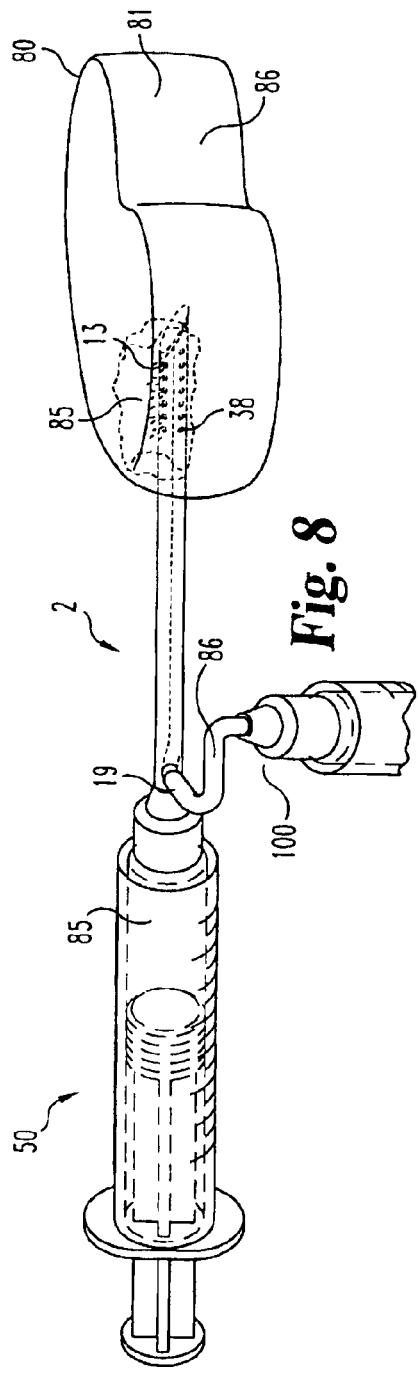
FIG. 8 is a side elevation view of the syringe needle assembly of FIG. 2 in use to simultaneously deliver and remove fluid material into and from an interior spinal disc space.

FIG. 8 shows the medical delivery device of FIG. 2B in use. After providing access to disc 80 (e.g. minimally invasive access as discussed above) a medical agent 85 is shown being delivered with needle assembly 2 through apertures 13 into the nucleus 81 of spinal disc 80 simultaneously with the withdrawal of material (e.g. tissue fluid) 86 through apertures 38, for example using a separate syringe device 100 coupled to connector 19. It will be understood that syringe device 100 could be replaced with a simple container that can collect fluid at ambient pressure in situations wherein the pressure generated in the disc or other tissue bed is sufficient to drive fluid and/or other tissue material through the withdrawal fluid path (i.e. assisted withdrawal with reduced pressure or other active mechanisms will not necessarily be required in all situations). Connector 19 can be adapted to be fitted with a flexible tubing or fitted with a special connector such as a luer-lock fitting to assist in creating a suitable pathway into syringe device 100 or another collection device.

Figure 9:
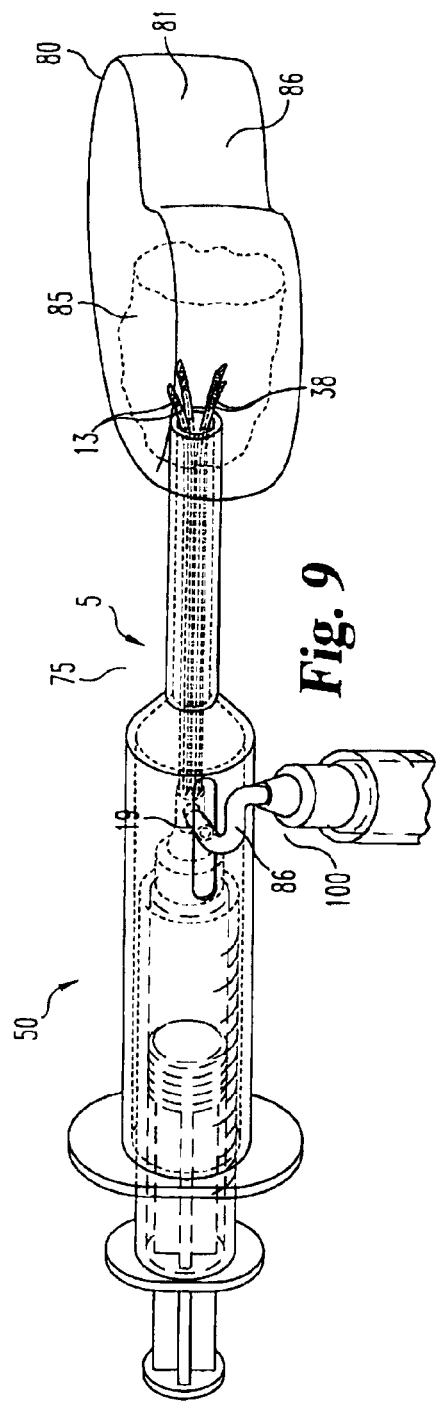
FIG. 9 is a side elevation view of the syringe needle assembly of FIG. 5G in use to deliver fluid material into interior spinal disc space.

FIG. 9 illustrates the syringe needle assembly of FIG. 5G in use. After providing minimally invasive or other access to disc 80, a medical agent 85 is shown being delivered with needle assembly 5 through apertures 13 into the nucleus 81 of spinal disc 80 simultaneously with the withdrawal of fluid 86 through apertures 38 and delivered into syringe 100 through connector 19. The elongated members 23 are engaged in cannulated member 75 having a plurality of lumens 76 which direct the elongated members 23 according to a desired delivery pattern. To achieve delivery, the end of cannulated member 75 can be docked or positioned against the disc annulus while the elongated penetrating members 23 are fully received in sleeve 75. The syringe-needle assembly (50 and 5) can then be advanced into sleeve 75 to drive the penetrating members 23 through their respective curved lumens, out the end of sleeve 75, through the disc annulus, and into the nucleus 81. The sleeve 75 with its curved lumens allows penetration of the disc annulus in a defined, relatively small region, but directs the members 23 to a desired, differing pattern, such as a more spaced pattern, a directional pattern deflected from the longitudinal axis of the sleeve 75 (e.g. to the right, the left, up or down), a radial pattern, etc. After delivery of the medical agent is complete, the syringe needle assembly can be pulled back through cannulated member 75 to withdraw members back into their respective, dedicated lumens, and the overall device removed from the operational field.

Figure 10:
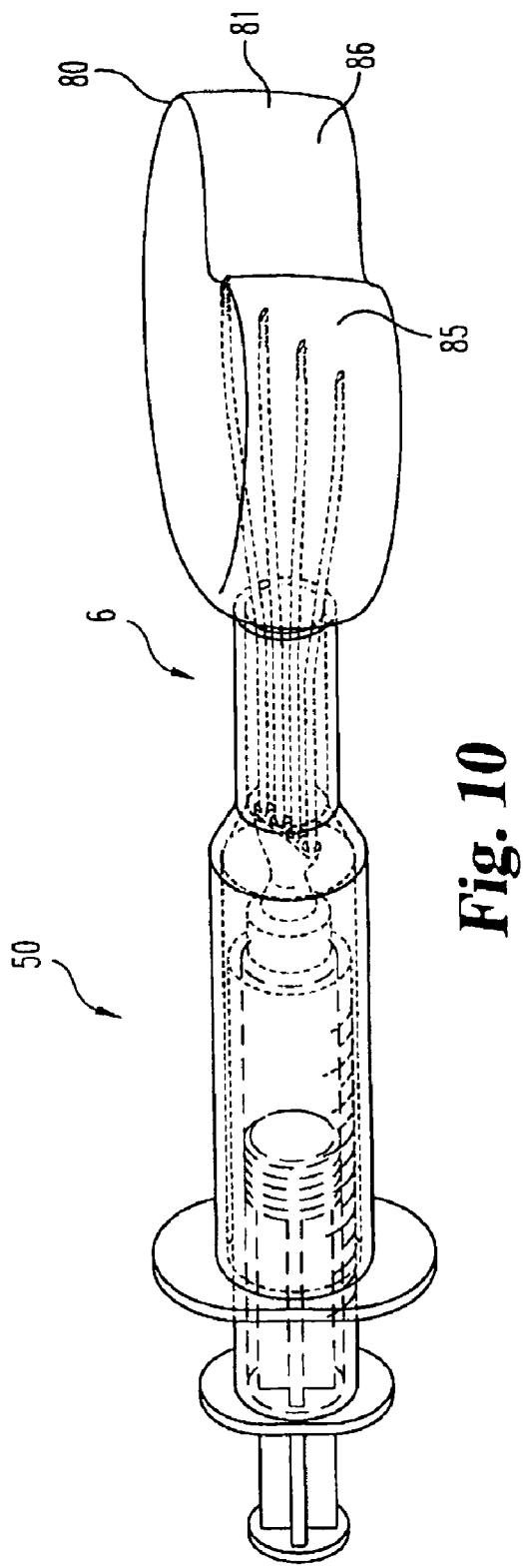
FIG. 10 is a side elevation view of the syringe needle assembly of FIG. 6 in use to deliver fluid material into interior spinal disc space.

FIG. 10 shows the medical delivery device of FIG. 6 in use. After providing access to disc 80, a medical agent 85 is shown being delivered with needle assembly 6 through apertures 13 into the nucleus 81 of spinal disc 80. The elongated members 23, constructed from a biocompatible material having shape memory properties are engaged in sleeve 75 having a single lumen 76. When fully engaged within sleeve 75, the elongated members 23 are constrained together and as they are expelled during insertion into spinal disc 80 they separate, regaining their original, wider conformation to deliver the therapeutic agent according to a predetermined delivery pattern. Again, to achieve delivery, the sleeve 75 can be positioned against the disc annulus with the elongated members 23 fully received therein, whereafter the members can be ejected from the sleeve 75 to penetrate the annulus and enter into the nucleus pulposus tissue within. The medical agent can then be delivered from the elongated members 23 by actuation of the syringe plunger, whereafter the members 23 can be retracted back into sleeve 75, and the delivery device removed from the operational field.

Figure 11:
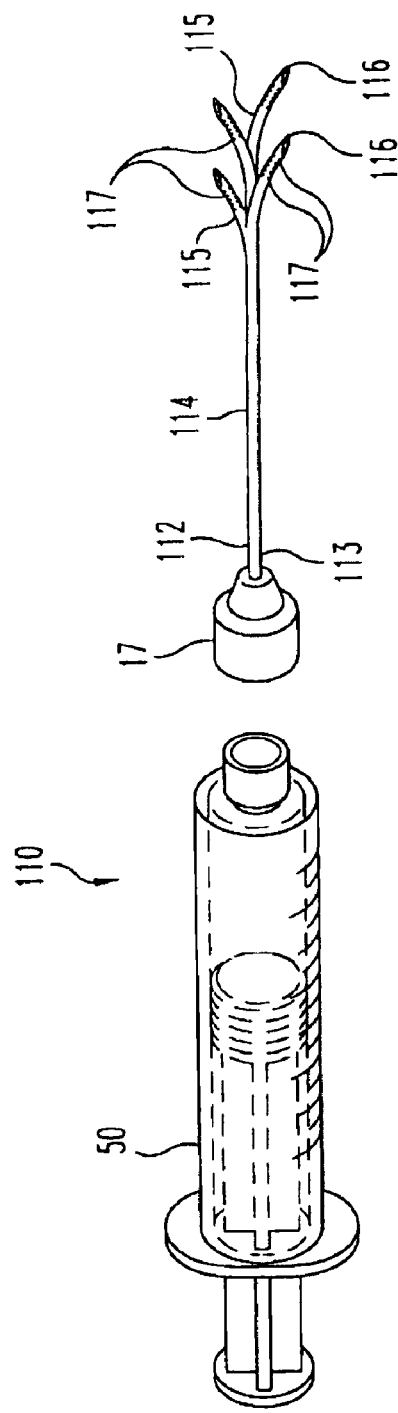
FIG. 11 is a side elevation view of another syringe needle assembly of the present invention.

With reference to FIG. 11, shown is another medical delivery device 110 of the invention. Device 110 includes a syringe 50 as previously described, and a needle assembly 112. Needle assembly 112 includes a connector 17 for fluid connection to syringe 50, and a branching elongated needle 113. Branching needle 113 includes a straight portion 114 having an internal lumen that is common to and feeds a plurality of branching needle portions 115 which extend arcuately and radially away from the longitudinal axis of the straight portion 114. Each branching portion 115 includes a tissue penetrating tip 116, and a plurality of sidewall 117 for delivery of a medical agent. Tissue penetrating tips 116 can be open, but are preferably closed to facilitate advantageous flow of medical agent out of sidewall orifices 117. In advantageous embodiments, branching elongated needle 114 is constructed of a resilient material such that branching portions 115 can be constrained to a smaller overall profile for delivery into a spinal disc or other tissue region, potentially within single lumen sleeve members (e.g. 75) as described hereinabove, which sleeve members may incorporate tissue penetrating tips for facilitating penetration to a desired tissue level for launch of the needles (e.g. 114) received therein.

Figure 12A:
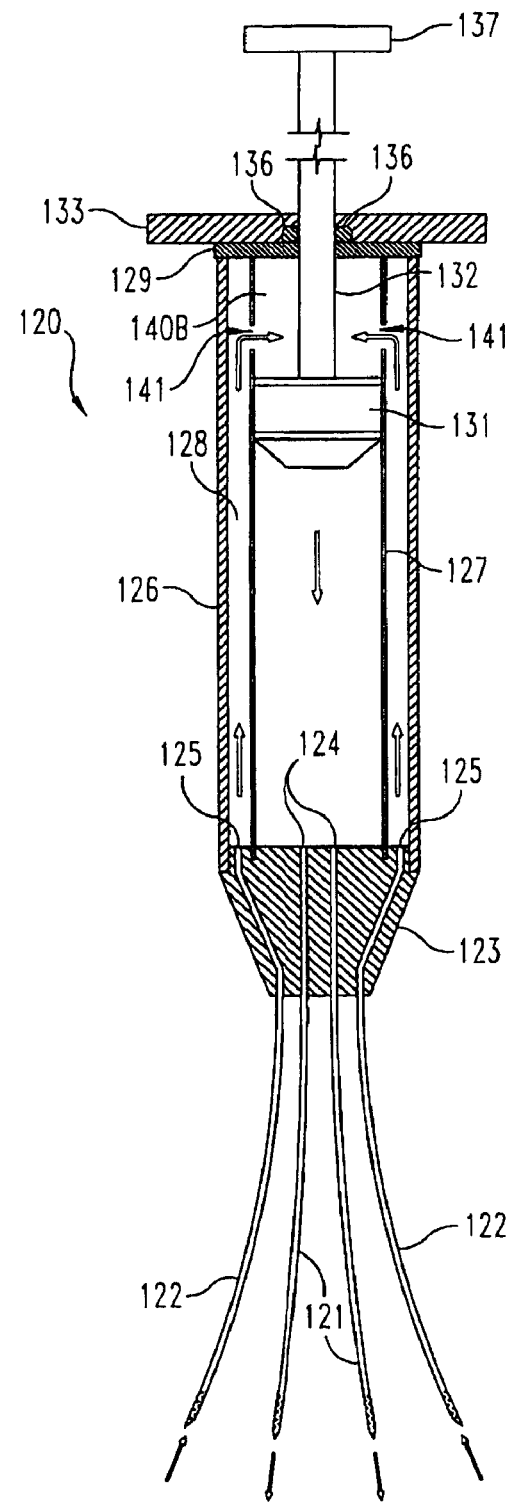
FIG. 12A is a midline cross-sectional view of a syringe needle assembly of the invention configured to inject and remove material simultaneously upon the actuation of a single plunger.
Figure 12B:
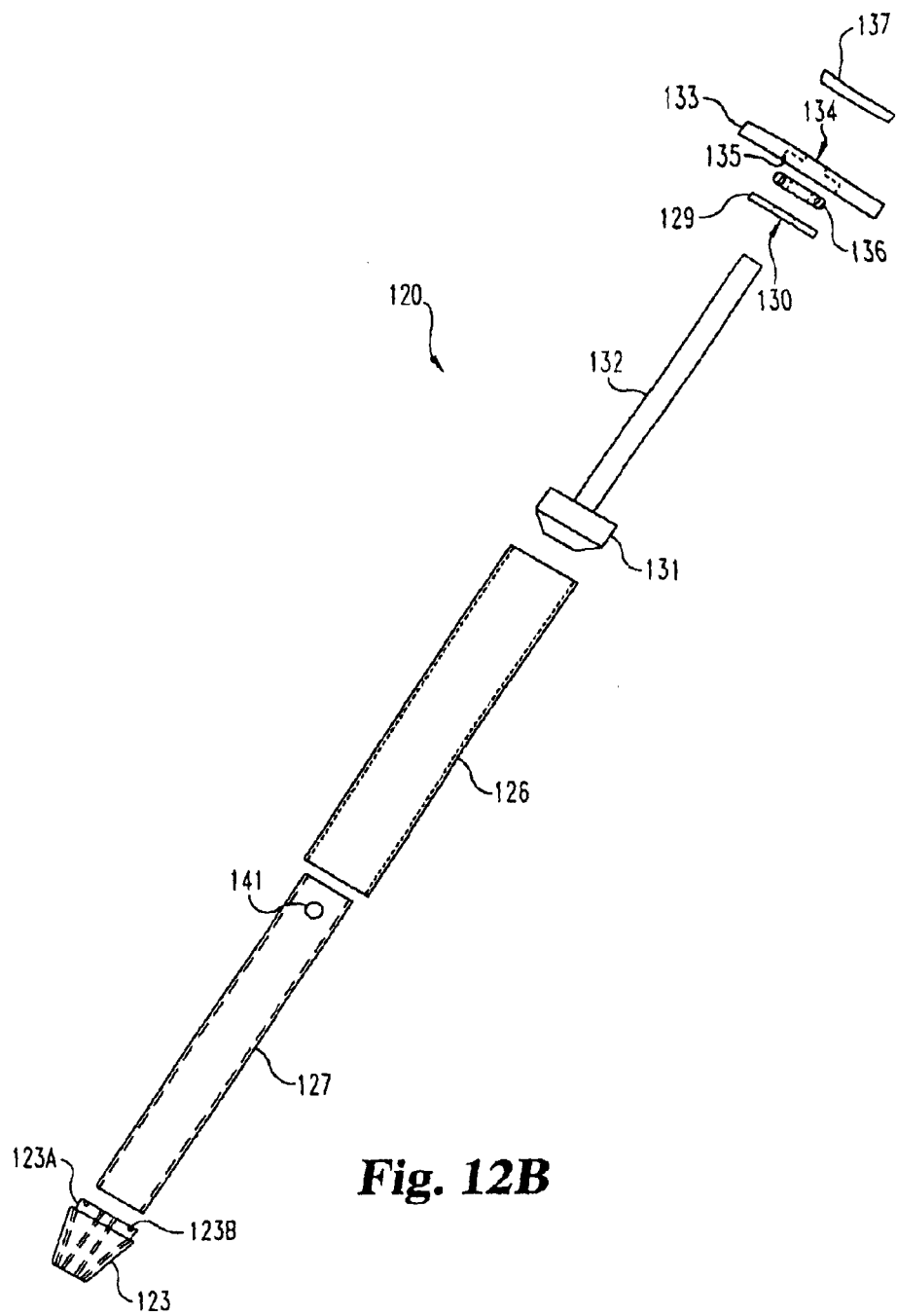
FIG. 12B is an exploded view of syringe of the syringe needle assembly of FIG. 12A.

With reference to FIGS. 12A and 12B, an further medical agent delivery device of the present invention will be described. The illustrated device 120 is configured to simultaneously deliver and withdraw material from patient tissue upon actuation of a single syringe plunger. Generally, in the illustrated device 120, medical agent forward of an advancing plunger head will be expelled through one or more first fluid paths, and material such as fluid from within tissue of the patient will be withdrawn though one or more second fluid paths coupled to and activated by a negative pressure zone generated rearward of the advancing plunger head (see, generally, arrows in FIG. 12A illustrating material flow directions). In this manner, a simple operation can be performed to both deliver and withdraw material to and from patient tissue, and the delivered and withdrawn material will be of substantially the same volume since the volumetric displacement forward and rearward of the advancing plunger head will be similar.

Turning now specifically to the features of the drawings, delivery device 120 includes a plurality of needles 121 and 122 which, as shown, can include a curved configuration in a relaxed condition. Straight, deflectable or non-deflectable needles can also be used within the invention, as discussed above. Needles 121 and 122 have their distal ends received within a distal cap piece 123. Distal cap piece 123 defines a plurality of internal lumens 124 and 125 corresponding to and communicating with internal lumens of needles 121 and 122. Device 120 has a barrel portion defined by an outer cylindrical member 126 and an inner cylindrical member 127, which define a generally annular chamber 128 between them. The distal end of the outer cylindrical member 126 is sealingly received around shoulder portion 123A of distal cap member 123, while the distal end of inner cylindrical member 127 is sealingly received within an annular notch 123B defined within distal cap member 123.

At the proximal end of device 120, proximal cap member 129 having a central opening 130 is sealed against the proximal ends of outer and inner cylindrical members 126 and 127. The plunger apparatus includes plunger head 131 received within and cooperating with the internal walls of inner cylindrical member 127. Plunger arm 132 is connected to plunger head 131 and extends through central opening 130 in proximal cap 129. In the illustrated device 120, plunger arm 132 is either a hollow or solid cylinder, although other shapes can also be used within the invention. A proximal grip plate 133 is secured to the outer surface of proximal cap 129. Grip plate 133 includes a central opening 134 generally corresponding in size to the central opening 130 of proximal cap 129, and is grooved partially through its thickness about the opening to create an annular shoulder 135, which in turn creates an internal volume when the grip plate 133 is secured to the proximal cap 129. A sealing element such as an "O"-ring 136 is received within such internal volume, and cooperates to substantially maintain a pressure seal against plunger arm 132 as it is advanced into and withdrawn from the barrel of device 120. A push-pull handle element 137 is provided at the end of plunger arm 132 to facilitate manually advancing and withdrawing the plunger apparatus in and out of the device 120.

That portion of inner chamber 140A (defined by the internal volume of inner cylindrical member 127) forward of the plunger head 131 fluidly communicates with lumens 124 for delivery of a medical agent from forward chamber 140B through and out of delivery needles 121. Annular chamber 128 fluidly communicates with that portion of inner chamber 140B rearward of plunger head 131 through one or more openings 141 defined in inner cylindrical member 127. Annular chamber 128, in turn, fluidly communicates with peripheral lumens 125 defined in distal cap 123, which communicate with internal lumens of withdrawal needles 122. It will be understood that needles 121 and 122 can include a single opening at their distal end, and/or can include one or a plurality of sidewall openings 142 as in other needles disclosed hereinabove.

In operation, chamber portion 140A forward of plunger head 131 can be filled with a medical agent at manufacture, or just prior to delivery. The latter may be achieved, for example, by advancing the plunger head 131 to its forward-most position within inner cylindrical member 127, positioning the distal ends of delivery needles 121 into a volume of the medical agent, and drawing the plunger back up the inner cylindrical member 127 (but desirably stopping short of openings 141). Thereafter, the distal ends of needles 121 and 122 can be advanced into disc nucleus or other tissue for delivery, and plunger head 131 advanced distally within inner cylindrical member 127. In this manner, the medical agent will be delivered from forward chamber portion 140A through lumens 124 and out of sidewall openings 142 of delivery needles 121. At the same time, a negative pressure zone will be created rearward of the plunger 131 within rearward chamber portion 140B, and this negative pressure will be communicated through openings 141 into annular chamber 128, through lumens 125 and ultimately to sidewall openings 142 in withdrawal needles 122. Fluid or other tissue will thereby be withdrawn under pressure from the nucleus pulposus or other tissue, will fill into annular chamber 128, and if sufficient in volume will spill through holes 141 and into rearward chamber portion 140B occurring behind the now-advanced position of plunger head 131. After this, in one mode of use, needles 121 and 122 can be withdrawn from the patient tissue while leaving the plunger head in its advanced position after delivery of the medical agent.

It will be understood that a variety of other configurations can be used while achieving a simultaneous delivery and withdrawal of material as effectuated by device 120 of FIGS. 12A and 12B. For example, an inverse operation can be provided, wherein a medical agent to be delivered is originally loaded rearward of plunger head 131 in an advanced position and within annular chamber 128, and the plunger head 131 withdrawn proximally to force the agent out of needles 122 while simultaneously withdrawing material from needles 121. As well, separate plungers could be provided for separate, discrete chambers for withdrawal of material and delivery of material. In one mode, a first plunger could be advanced in a first chamber to deliver an agent through a first needle or needles of the assembly, while a second plunger is withdrawn through a second chamber to withdraw material from a second needle of the assembly. These and still other adaptations can be used within the ambit of the present invention.

In addition or as an alternative to relieving pressure created by delivered medical agent to tissue volumes, the withdrawal (including simultaneous and/or intermittent withdrawal) of patient fluid from adjacent tissue regions can potentially facilitate the creation of flow or diffusion gradients that assist in spreading or regionalizing the delivered agent. Thus, in certain instances, it will be desired to have withdrawal openings somewhat spaced from delivery openings on medical delivery devices of the invention. This spacing will also help to prevent or minimize withdrawal of amounts of the delivered agent when that is undesired. Such spacing may be achieved by having multiple needles with openings spaced from one another as in certain embodiments disclosed herein, and/or by having openings spaced from one another on a single needle having a bifurcated lumen, wherein one side of the bifurcation communicates with one or more delivery openings and the other communicates with one or more withdrawal openings. Spacing of delivery and withdrawal openings may be achieved for example by radial spacing and/or by longitudinal spacing along a single needle body.

Figure 13:
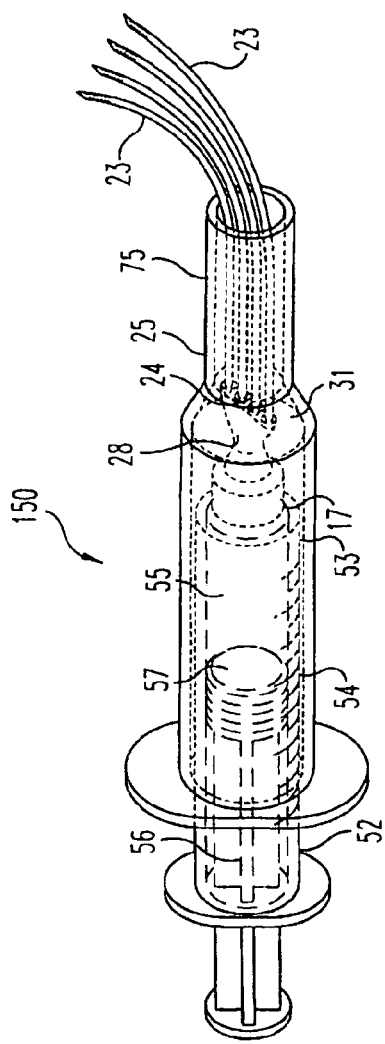
FIG. 13 illustrates another medical delivery device of the present invention.

Referring now to FIG. 13, shown is another medical delivery device 150 of the present invention. Device 150 is similar to the device depicted in FIGS. 6 and 10, except elongated members 23 have a relaxed condition in which they each curve to one direction away from the longitudinal axis of device 150 and provide a generally planar, laterally-facing ejection pattern. In this fashion, device 150 can be advanced to position sleeve 75 against the annulus fibrosus of a spinal disc, and elongated members 23 advanced out of sleeve, through the annulus fibrosus (or an opening already therein), whereafter upon further advancement they assume their original laterally-facing configuration for delivery of agent to one side of the interior disc space. The members 23 can thereafter be withdrawn back into sleeve 75, and either the sleeve/needle/syringe assembly rotated 180 degrees, or the needle/syringe assembly rotated within the sleeve 180 degrees. Advancement of the members 23 out of sleeve member 75 again thereafter enables delivery of amounts of the medical agent to the other side of the interior space of the disc.

Figure 14:
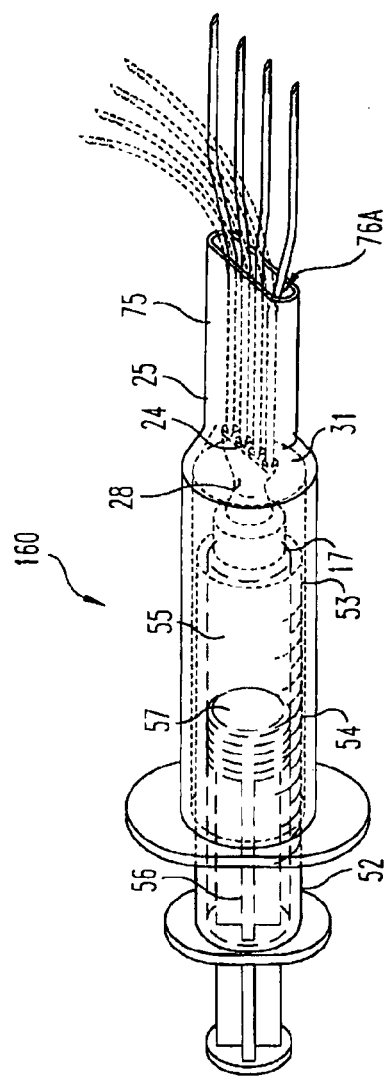
FIG. 14 illustrates another medical delivery device of 5 the present invention.

FIG. 14 depicts still another medical delivery device 160 of the present invention. Device 160 can have syringe-needle assemblies similar to those depicted in FIGS. 6 and 13. Device 160, however, includes a retraction sleeve having a modified, more flattened distal region and an elongated opening 76A such as an elongated ovate opening. Elongated opening 76A beneficially contributes to assuring that needles 23 remain in a substantially planar array. In this regard, needles 23 can be generally straight and provide a planar array, can include needles that flare but return to extend generally parallel to their original longitudinal axis (as shown in FIG. 15), can curve laterally to one side (shown in phantom in FIG. 15) or both sides, or any combination of these or other desired configurations.

The medical agent delivered to the patient using methods and devices of the present invention can be, for example, therapeutic or diagnostic. Diagnostic agents include, for example, imaging agents such as x-ray contrast agents, magnetic resonance imaging (MRI) agents, and the like. Therapeutic agents may include, for example, cells, including disc nucleus cells and/or adult or embryonic stem cells, drugs, anti-inflammatory agents, tissue growth factors, anesthetics, antibiotics, MMP inhibitors, extracellular matrix components, keratin-family proteins, platelet-rich plasma, bone marrow, morphogenic proteins including bone morphogenic proteins such as BMP-2 or BMP-7, nucleic acid constructs such as expression vectors including nucleic acid molecules encoding morphogenic proteins such as those mentioned above or LIM mineralization protein (LMP), and a wide variety of other known medical agents. Such medical agents can be delivered in certain embodiments in controlled release fashion, for example by the injection of suspensions of controlled release particles such as controlled release microspheres which are deposited within the recipient tissue (e.g. disc nucleus pulposus tissue) for sustained release of the medical agent.

Figure 15B:
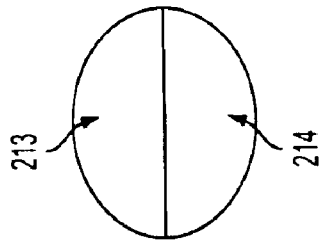
Figure 15A:
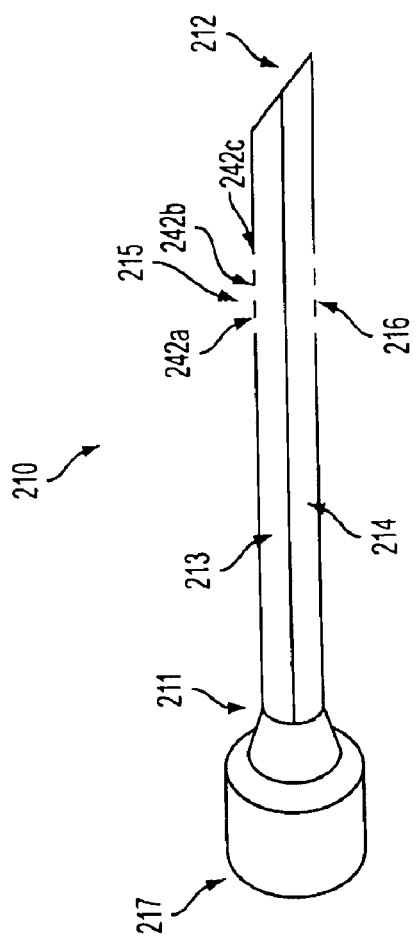
FIG. 15a presents one embodiment of a needle for injection of therapeutic fluid into a joint space.

With reference to FIGS. 15a and 15b, an embodiment of a needle for injecting therapeutic fluid into a target space is illustrated. The term "target space" as referred to herein means anatomical space within a patient (human or otherwise), such as, a joint, a blood vessel, a body cavity, and so on. The term therapeutic fluid means any flowable substance that may prevent, treat, or alleviate signs or symptoms of the disease or condition. The term therapeutic fluids includes, but is not limited to, solutions, syrups, dispersions, suspensions, emulsions, lotions, gels, creams, slurries, flowable polymers, hydrogels, and so forth.

The needle 210 includes one or more elongated non-coring tissue-penetrating members formed of a biocompatible material for penetrating into a target space and has a proximal end 211 and a distal end 212. The proximal end 211 may include at least one connector, described below, for connecting the needle 210 to an infusion device, such as, an infusion device, a pump, a catheter, and so forth. Preferably, the needle 210 is a hypodermic needle with the distal end adapted to be capable of penetrating a target space. Accordingly, the needle is preferably made of rigid material, such as surgical steel or rigid plastic, with the distal end comprising a cutting edge, such as a bevel, adapted to pierce through a patient's skin or other tissue, such as a joint capsule, to enter the target space. Although the needle 210 may be inserted into the target space using a guide channel, such as a guide wire or a cannula, in the preferred embodiments the needle 210 may be used to pierce the target space without any additional instruments.

The needle 210 further comprises at least one extraction orifice and at least one injection orifice located on said one or more tissue-penetrating members and are in fluid communication with an extraction fluid path and injection fluid path, respectively. The at least one injection orifice is positioned remotely from the at least one extraction orifice. The lumens 213 and 214 are adjacent to each other in the embodiment shown in FIG. 15a, although other variations are possible. Each lumen may comprise a single lumen or multiple lumens which may or may not be in fluid communication with each other.

At least one extraction orifice and at least one injection orifice may be formed in the sidewalls at or proximally to the distal ends of their respective lumens. In addition to or instead of these sidewall orifices, the extraction lumen, injection lumen, or both may include orifices at their distal ends. In some embodiments, the needle 210 may include one or more obtuators plugging the orifices during the insertion of the needle into a target space to prevent the orifices from plugging up with tissue.

The one or more extraction orifices may be used to extract target space content, such as target space fluids, catabolic tissue fluids, target space tissue, native degenerative factors and so forth, from the target space, whereas the one or more injection orifices may be used to inject a therapeutic fluid into the target space. Extracting target space contents from the target space may allow for injection of a larger volume of the therapeutic fluid and may flush out natural degenerative factors making the treatment more effective. Preferably, the one or more extraction orifices and the one or more injection orifices are remote from each other to avoid or, at least, to minimize extracting the therapeutic fluid from the target space.

In addition, since the needle is used to exchange fluids in a stagnant environment, the orifices may be designed to create pressure gradients within the target space. The number of orifices, their size and their positions relative to each other may be varied to create one or more pressure gradients to force the target space contents to flow from one area of the target space to another making room for injection of therapeutic fluid into the target space. Pressure gradients may also facilitate an uniform diffusion of the therapeutic fluid throughout the target space. In embodiments when exchanging viscous materials, it may be advantageous to have multiple extraction and multiple injection orifices to create localized pressure gradients which may further improve distribution of the therapeutic fluid in the target space.

Location of the one or more extraction orifices and one or more injection orifices depends on the type of target space being treated, and more specifically, the target space content's characteristics. For example, if the instant needle is used for replacing or augmenting nucleus pulposus, because the injected fluid is relatively viscous and, thus, cannot diffuse quickly, the orifices can be closer to each other than if the needle is used for exchanging fluids in a knee joint because the knee joint fluids are generally less viscous. More specifically, the orifices may be located only about 1 to about 5 mm apart when exchanging fluids in a disc, whereas the orifices may be located about 5 to about 20 mm apart when exchanging fluids in a knee joint. Furthermore, when replacing viscous fluids or dense tissue, multiple extraction and injection orifices may be desirable to provide for a more uniform distribution of the therapeutic fluid.

The needle design is such that the one or more extraction orifices can remove fluid through the surrounding tissues via diffusion through the tissues at a rate which allows injection of the therapeutic fluid into the same tissues. In other words, there is an approximately equivalent volumetric exchange of catabolic tissue fluids with the therapeutic fluids. Target spaces, and joints in particular, are normally fully hydrated making injection of additional therapeutic fluids into them difficult, if not impossible. Therefore, some target space content may need to be removed at the same or faster rate than the therapeutic agent being injected into the target space. If the rate of injection is faster, the excess therapeutic agent may leak out of the target space during injection and flow into unwanted locations. For example, if, when injecting therapeutic fluid into a disc joint, the disc fluid is extracted at about 1 cc/min, the therapeutic fluid may be injected into the disc space at about 1 cc/min or slower. Injecting the therapeutic fluid at a faster rate may result in an overflow of the therapeutic fluid from the disc space into the spinal canal. The fluid in the spinal canal is likely to exert pressure on the spinal cord causing pain to the patient.

The size and number of the orifices may depend on the type of the target space being treated. Since, a larger amount of fluid may need to be delivered to a larger target space, larger holes and/or more holes may be necessary to minimize the duration of the procedure. In addition, larger holes may be desirable when viscous fluids are being extracted or injected. Lastly, larger number of holes may ensure that the therapeutic fluid is more thoroughly distributed throughput the target space or may ensure a more even extraction of the native fluid from the target space. By way of a non-limiting example, the orifices may be about 0.05 mm to about 1 mm in diameter and about 1 mm to about 5 mm apart when exchanging fluids in an intervertebral disc and may be about 0.5 mm to about 3 mm in diameter and about 5 mm to about 20 mm apart when exchanging fluids in a knee joint.

Referring to FIG. 15a, in one non-limiting embodiment, a sidewall orifice 215 of the instant needle 210 may comprise a series of orifices 215a, 215b, 215c. As explained above, it is desirable to create pressure gradients within the target space which may facilitate a more uniform diffusion of the therapeutic fluid throughout the target space. Accordingly, the diameter of these orifices may be progressively varied to create the desired pressure gradient. For example, if the pressure gradient that aids diffusion of the therapeutic fluid from the center to the periphery of the target space is preferred, the diameter of the orifices of the one or more extraction orifices may progressively increase toward the proximal end 243 of the needle 240, that is, the diameter of the orifice 242a is larger that the diameter of the orifice 242b which is, in turn, larger than the diameter of the orifice 242c. In such embodiment, the therapeutic fluid may be injected through a distal end of the injection lumen into the center of the target space or through a sidewall injection orifice with a orifice size changes in a reverse order so that more fluid is injected in the center of the target space further increasing the gradient between the center and periphery. If a pressure gradient that aids diffusion of the therapeutic fluid from the periphery to the center of the target space is preferred, the diameter of the orifices of the sidewall extraction orifice may progressively decrease toward the proximal end of the needle, while the diameter of the orifices of the sidewall injection orifice may progressively increase toward the proximal end of the needle. Additionally or alternatively, the target space fluid may be extracted from the distal end of the extraction lumen.

Figure 16B:
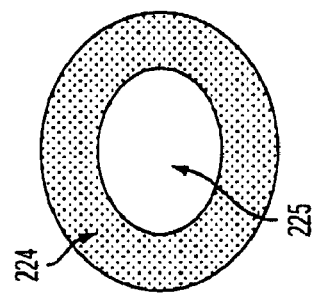
Figure 16A:
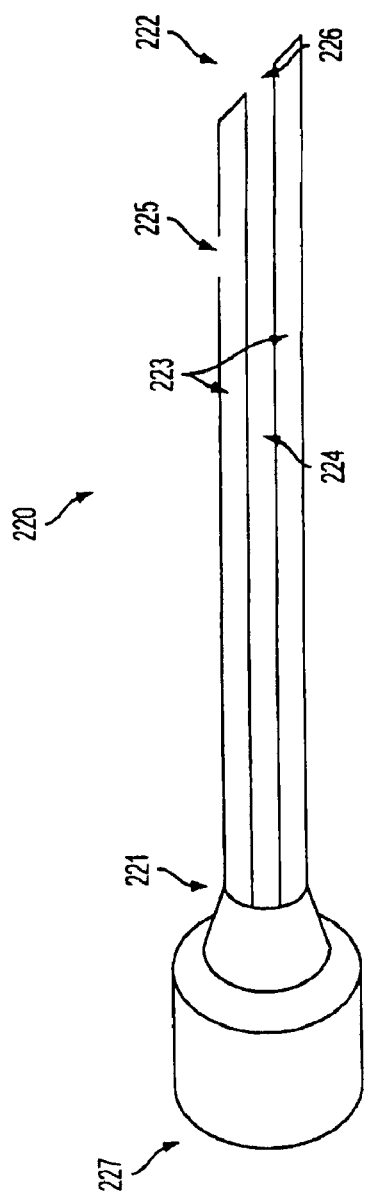
FIG. 16a presents another embodiment of the instant needle.

Another embodiment of the instant needle 220 for delivering a therapeutic fluid to a target space is shown in FIGS. 16a and 16b. Compared to the needle 210, the fluidly isolated lumens 223 and 224 are in a concentric relation with each other. Similarly to the needle 210, the needle 220 includes a proximal end 221 having at least one connector and a blunt or sharp distal end 222. The outside lumen 223 may have one or more orifices 225 in its sidewall or at its distal end (not shown), whereas the inside lumen 224 has one or more orifices 226 at the distal end 222. As in the embodiments described above, the extraction orifice and the injection orifice are remote from each other to prevent or, at least, to minimize extraction of the therapeutic fluid from the target space. The outside lumen may have multiple orifices located along both the longitudinal and radial directions.

Relative position of the extraction lumen or the injection lumen to each other depends on the desired direction of the pressure gradients. For example, if the pressure gradient forcing fluids in the center of the target space to flow towards the periphery is desired, the outside lumen may be used as an extraction lumen. On the other hand, if the pressure gradient forcing fluids to flow from the periphery of the target space to the center is desired, the outside lumen may be used as an injection lumen. In preferred embodiments, the outside lumen is used as an extraction lumen so that the therapeutic fluid is injected into the center of the target space.

In operation, the instant needle may be connected to an infusion device, such as a infusion device, a catheter, or a pump. The needle may be an integral part of the infusion device or may be connected to the device using a connector. In one embodiment, a multi-chamber infusion device, catheter or pump may be utilized. Such infusion device, catheter, or pump may include an extraction chamber and an injection chamber that are fluidly isolated from each other. Each chamber may, in turn, comprise a single chamber or multiple chambers that may or may not be fluidly connected among each other. When a multi-chamber infusion device, catheter, or pump is connected to the instant needle, its chambers are in fluid communication with the corresponding lumen of the needle. Alternatively, multiple independent catheters, infusion devices or pumps may be connected to the instant needle, some of which will be in fluid communication with the extraction lumen of the needle to be used for extraction of the target space content while others will be in fluid communication with the injection lumen of the needle to be used for injecting fluid into the target space.

In some embodiments, the needle may be removably connected to an infusion device through one or more connectors. Such connectors are known in the art and may employ, for example, a gasket or the like to form a fluidic pathway between the lumens of the needle and the corresponding chambers of the infusion device connected to the needle and to ensure that such fluidic pathways remain isolated from each other. Additionally or alternatively, a male-female connection could be employed between the needle and the infusion device or the catheter. Finally, any other type of connector known to one skilled in the art may be used to secure the needle to the infusion device or to the catheter as long as the extraction and injection lumen line up with the corresponding chambers or lumens to form isolated fluidic pathways. Some suitable examples are disclosed in, for example, U.S. Pat. No. 7,347,458.

Figure 17:
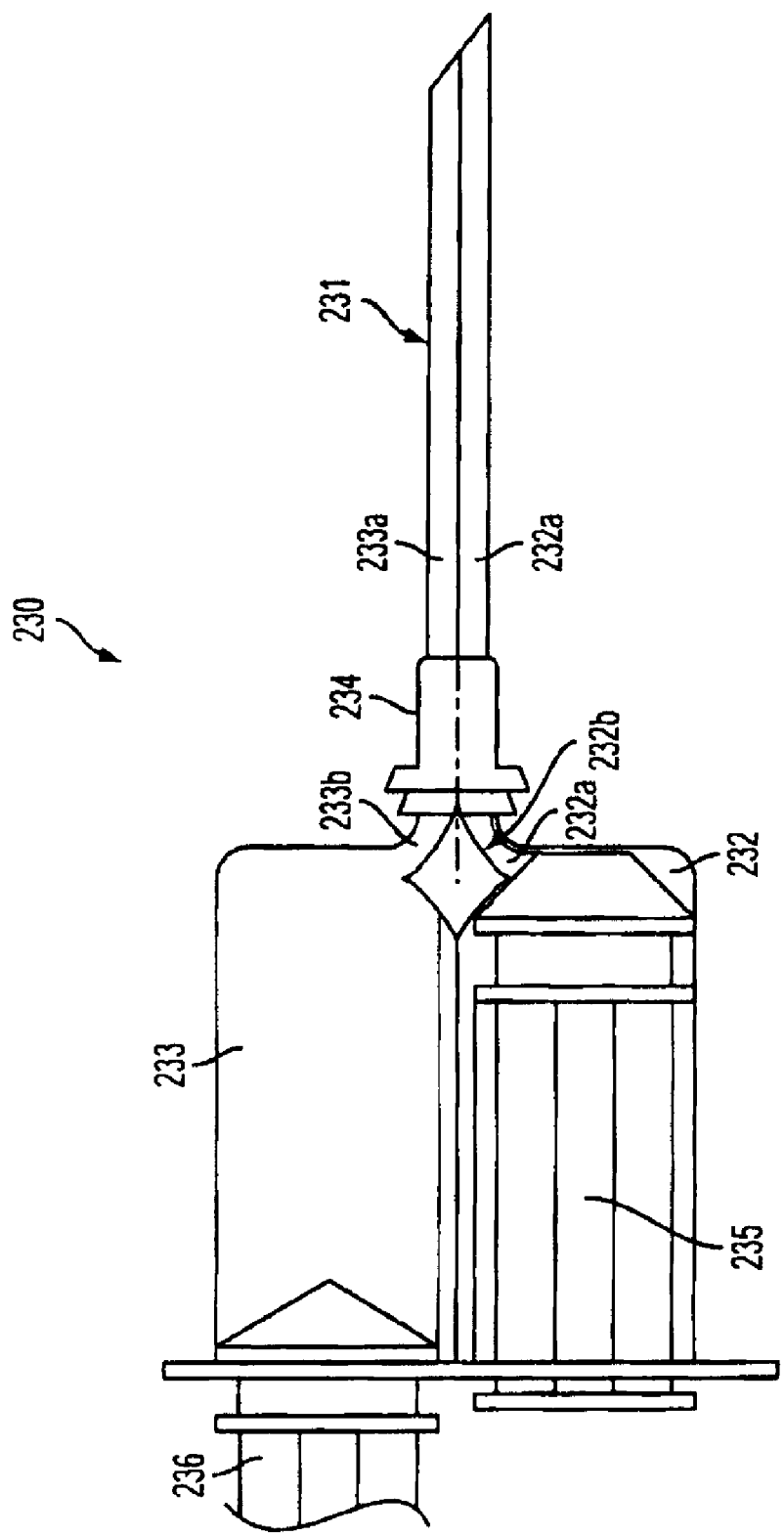
FIG. 17 presents an embodiment of a multi-chamber infusion device connected to the needle shown in FIG. 15.

FIG. 17 presents a non-limiting example of a multi-chamber infusion device 230 connected to the instant needle 231 using a connector 234. Alternatively, the needle 231 may be an integral part of the infusion device 230. The body of the infusion device may be formed from any known material of which infusion devices of the prior art are normally manufactured, preferably plastic or glass. The infusion device 230 may comprise an extraction chamber 232 and an injection chamber 233 that are fluidly isolated from each other. The extraction chamber 232 is fluidly connected to an extraction lumen 232a of the needle 231 via an extraction channel 232b. Similarly, the injection chamber 233 is in fluid communication with an injection lumen 233a of the needle 231 via the injection channel 233b. Although an embodiment of the needle with adjacent lumens is shown in FIG. 17, it will be understood that any other embodiment, such as, an embodiment where the lumens are in concentric relationship, may also be used.

The extraction chamber 232 may hold the fluid extracted from the target space, whereas the injection chamber may hold the therapeutic fluid to be injected into the target space. The chambers may share a common wall, as shown in FIG. 17, or may be completely independent of each other. In addition, they may be connected by a bracket or other suitable forms of attachment to keep them in relative position of each other.

Furthermore, each chamber includes a plunger, referred to herein as an extraction plunger 235 or an injection plunger 236 respectively. The plungers may be standard infusion device plungers as would be found in single chamber infusion devices well known in the art. The plungers move independently of each other. In FIG. 17, the injection chamber 233 is shown loaded with the therapeutic fluid and with the injection plunger 236 in a fully proximal position. The therapeutic fluid may be injected into the target space by moving the injection plunger distally. On the contrary, the extraction plunger is shown in the most distal position and, by pulling the extraction plunger proximally, the target space content may be extracted from the target space into the extraction chamber of the infusion device.

In another aspect, a method of delivering therapeutic fluid to a target space is provided. Initially, the extraction chamber of an infusion device may be emptied while the injection chamber of the infusion device may be loaded with therapeutic fluid in preparation for the procedure. The needle may be inserted into the joint space using any known technique by itself or with the aid of a guidewire. The insertion and positioning of the needle may be performed under radiographic or image guided control to verify proper positioning inside the joint space. Once the needle is inserted into the target space, at least a portion of the target space content is extracted from the target space, thus creating a pressure gradient as described above. To extract at least a portion of the target space content, a negative pressure is created in the extraction chamber to draw the target space content through the one or more extraction orifices and extraction lumen into the extraction chamber. Concurrently or sequentially, a positive pressure is created in the injection chamber forcing the therapeutic fluid from the infusion chamber through the injection lumen and injection orifice into the target space.

As explained above, the needle is designed to extract the target space fluid or hydrated target space tissue while replacing it with therapeutic fluid. This method may allow for the introduction of a larger volume of therapeutic agent, a larger distribution of therapeutic agent, and flushing out of natural degenerative factors making the treatment more effective.

The therapeutic fluid may also include anti-inflammatory compounds both steroidal and non-steroidal, analgesics, antibiotic and antibacterial agents. Suitable non-limiting examples of steroidal anti-inflammatory compounds are corticosteroids such as hydrocortisone, cortisol, hydroxyltriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, difluorosone diacetate, fluocinolone, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone. Mixtures of the above steroidal anti-inflammatory compounds can also be used.

Non-limiting examples of non-steroidal anti-inflammatory compounds include nabumetone, celecoxib, etodolac, nimesulide, apasone, gold, oxicams, such as piroxicam, isoxicam, meloxicam, tenoxicam, sudoxicam, and CP-14,304; the salicylates, such as aspirin, disalcid, benorylate, trilisate, safapryn, solprin, diflunisal, and fendosal; the acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; the fenamates, such as mefenamic, meclofenamic, flufenamic, niflumic, and tolfenamic acids; the propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; and the pyrazoles, such as phenylbutazone, oxyphenbutazone, feprazone, azapropazone, and trimethazone.

The variety of compounds encompassed by the anti-inflammatory group of agents are well-known to those skilled in the art. For detailed disclosure of the chemical structure, synthesis, side effects, etc. of non-steroidal anti-inflammatory compounds, reference may be made to standard texts, including Anti-inflammatory and Anti-Rheumatic Drugs, K. D. Rainsford, Vol. I-III, CRC Press, Boca Raton, (1985), and Anti-inflammatory Agents, Chemistry and Pharmacology 1, R. A. Scherrer, et al., Academic Press, New York (1974). Mixtures of these non-steroidal anti-inflammatory compounds may also be employed, as well as the pharmacologically acceptable salts and esters of these compounds.

In some embodiments, analgesics may also be included. Analgesics may comprise, without limitation, non-steroid anti-inflammatory drugs, non-limiting examples of which have been recited above. Further, analgesics also include other types of compounds, such as, for example, opioids (such as, for example, morphine and naloxone), local anaesthetics (such as, for example, lidocaine), glutamate receptor antagonists, adenosine, canabinoids, cholinergic and GABA receptors agonists, and different neuropeptides. A detailed discussion of different analgesics is provided in Sawynok et al., (2003) Pharmacological Reviews, 55:1-20.

Suitable examples of antibiotics and antibacterial agents include, but are not limited to, amikacin, gentamicin, kanamycin, neomycin, netilmicin, paromomycin, streptomycin, tobramycin and apramycin, streptovaricins, rifamycins, amoxicillin, ampicillin azlocillin, carbenicillin, cloxacillin, dicloxacillin, flucloxacillin, mezlocillin, nafcillin, piperacillin, pivampicillin, ticarcillin, cefacetrile, cefadroxil, cefalexin, cefaloglycin cefalotin, cefapirin cefazolin, cefradine, cefaclor, ceforanide, cefotiam cefprozil, cefuroxime, cefdinir, cefditoren, cefixime cefinenoxime, cefoperazone cefotaxime, cefpiramide, cefpodoxime, ceftazidime, ceftibuten, ceftriaxone, cefepime, cefquinome, sulbactam, tazobactam, clavulanic acid, ampicillin/sulbactam (sultamicillin), co-amoxiclav and combinations thereof.

The instant needle may also be used to deliver anabolic treatment agents to a target space. Anabolic treatment agents may comprise one or more anabolic steroids, including but not limited to, androstenediol, methandrostenolone, methenolone, androstenedione, boldenone, chlorotestosterone (4-chlortestosterone), mibolerone, clostebol, dehydrochlormethyltestosterone, methyltestosterone, methandriol, nandrolone, dehydroepiandrosterone (DHEA), norandrostenediol, dihydrotestosterone (DHT), norandrostenedione, norethandrolone, dromostanolone, Drostanolone, epitrenbolone, ethylestrenol, fluoxymesterone, formebulone, gestrinone, mesterolone, methandienone, methandranone, oxandrolone, oxymesterone, oxymetholone, stanolone, stanozolol, testolactone, testosterone, tetrahydrogestrinone (THG), trenbolone or combinations thereof. In addition, anabolic treatment agents may include BMPs, GDFs, PDGFs, MMP inhibitors, cells, stem cells and combinations thereof.

The instruments and methods described above are particularly suitable for delivering therapeutic fluids to joint spaces such as knee joints and intervertebral discs. In one non-limiting embodiment, a nucleus pulposus of a degenerated intervertebral disc may be replaced or supplemented with a tissue bulking material that preserves the movement in the intervertebral joint. A wide variety of biocompatible polymeric materials may be used as a tissue bulking material.

They may include, but are not limited to, elastic materials, such as elastomeric materials, hydrogels or other hydrophilic polymers, or composites thereof. Suitable elastomers include silicone, polyurethane, copolymers of silicone and polyurethane, polyolefins, such as polyisobutylene and polyisoprene, neoprene, nitrile, vulcanized rubber and combinations thereof. Suitable hydrogels include natural hydrogels, and those formed from polyvinyl alcohol, acrylamides such as polyacrylic acid and poly(acrylonitrile-acrylic acid), non-resorbable polyurethanes, polyethylene glycol, poly(N-vinyl-2-pyrrolidone), acrylates such as polyacrylates, poly(2-hydroxy ethyl methacrylate), methyl methacrylate, 2-hydroxyethyl methacrylate, and copolymers of acrylates with N-vinyl pyrrolidone, N-vinyl lactams, acrylamide, polyurethanes and polyacrylonitrile, or may be other similar materials that form a hydrogel. The hydrogel materials may further be cross-linked to provide further strength to the implant. Examples of polyurethanes include thermoplastic polyurethanes, aliphatic polyurethanes, segmented polyurethanes, hydrophilic polyurethanes, polyether-urethane, polycarbonate-urethane and silicone polyether-urethane. Other suitable hydrophilic polymers include naturally-occurring materials such as glucomannan gel, polyphosphazenes, hyaluronic acid, polysaccharides, such as cross-linked carboxyl-containing polysaccharides, alkyl celluloses, hydroxyalkyl methyl celluloses, sodium chondroitin sulfate, cyclodextrin, polydextrose, dextran, gelatin, and combinations thereof.

Other suitable examples include materials that cure or polymerize in situ including elastomer, hydrogel, or rigid polymer materials, some of which are disclosed above. Additional suitable elastomers may include silicone elastomers, polyurethane elastomers, silicone-polyurethane copolymers, polyolefin rubbers, butyl rubbers, or combinations thereof. Additional suitable hydrogels may include polysaccharides, proteins, polyphosphazenes, poly(oxyethylene)-poly(oxypropylene) block polymers, poly(oxyethylene)-poly(oxypropylene) block polymers of ethylene diamine, poly (acrylic acids), poly(methacrylic acids), copolymers of acrylic acid and methacrylic acid, poly(vinyl acetate), sulfonated polymers, or combinations thereof. Additional suitable rigid polymers may include polymethylmethacrylate, silicones, polyurethanes, polyvinyl alcohol, polyamide, aromatic polyamide, polyether, polyester liquid crystal polymer, ionomer, poly(ethylene-co-methacrylic) acid, PBT (polybutylene terephthalate), polycarbonate, or combinations thereof. One commercially available example of in situ curable gel is Biocure by Medtronic Sofamor Danek, Memphis, Tenn.

Other suitable examples of the bulking materials include lightly cross-linked biocompatible homopolymers and copolymers of hydrophilic monomers such as 2-hydroxyalkyl acrylates and methacrylates, N-vinyl monomers, and ethylenically unsaturated acids and bases; polycyanoacrylate, polyethylene oxide-polypropylene glycol block copolymers, polygalacturonic acid, polyvinyl pyrrolidone, polyvinyl acetate, polyalkylene glycols, polyethylene oxide, collagen, sulfonated polymers, vinyl ether monomers or polymers, alginate, polyvinyl amines, polyvinyl pyridine, and polyvinyl imidazole. One can also use superabsorbent polymers (SAP) with or without additives. Superabsorbent polymers may include polymer chains that are synthetic, natural, and hybrid synthetic/natural polymers. Exemplary superabsorbent polymers may include, but are not limited to, polyacrylic acid, polymethacrylic acid, polymaleic acid, copolymers thereof, and alkali metal and ammonium salts thereof; graft copolymers of starch and acrylic acid, starch and saponified acrylonitrile, starch and saponified ethyl acrylate, and acrylate-vinyl acetate copolymers saponified; polyvinylpyrrolidone, polyvinyl alkylether, polyethylene oxide, polyacrylamide, and copolymers thereof; copolymers of maleic anhydride and alkyl vinylethers; saponified starch graft copolymers of acrylonitrile, acrylate esters, vinyl acetate, and starch graft copolymers of acrylic acid, methyacrylic acid, and maleic acid; the product of crosslinking acrylamide with backbones of kappa-carrageenan and sodium alginate using methylenebisacrylamide and potassium persulfate; and the product of crosslinking, using a bifunctional crosslinking reagent, an acyl-modified protein matrix such as soy protein isolate which has been acyl-modified by treatment with ethylenediaminetetraacetic acid dianhydride; mixtures and combinations thereof. Further, one can use silicone-based materials, polyethylene terephthalate, polycarbonate, thermoplastic elastomers and copolymers such as ether-ketone polymers such as poly(etheretherketone.

Alternatively, the disc may be removed and adjacent vertebrae may be fused together by a procedure known as interbody fusion. The materials, referred to as fusion disc materials, provide scaffolding through and around which the patient's new bone can grow, gradually replacing these materials as the adjacent vertebrae fuse. Some examples of materials suitable for interbody fusion include, but are not limited to, flowable growth factor carriers, such as polysaccharides, proteins and polypeptides, glycosaminoglycans, proteoglycans, collagen, elastin, hyaluronic acid, dermatan sulfate, chitin, chitosan, pectin, (modified) dextran, (modified) starch, or mixtures or composites thereof. In addition, injectable matrices include Norian® SRS® Bone Void Filler, Synthes, West Chester, Pa.; CORTOSS® Injectable Synthetic Bone Filler, Orthovita, Malvern, Pa.; and Cerament Bone Void Filler, Bone Suporifice AB, Sweden. Other materials that are suitable as matrices include Any suitable bone cement including, but not limited to, acrylic based bone cement, pastes comprising bone particles, or ceramic based cements may be used. Preferably, a low-viscosity liquid bone cement is employed. Synthetic polymers may also be employed, including for example biodegradable synthetic polymers such as polylactic acid, polyglycolide, polylactic polyglycolic acid copolymers ("PLGA"), polycaprolactone ("PCL"), poly(dioxanone), poly(trimethylene carbonate) copolymers, polyglyconate, poly(propylene fumarate), poly(ethylene terephthalate), poly(butylene terephthalate), polyethyleneglycol, polycaprolactone copolymers, polyhydroxybutyrate, polyhydroxyvalerate, tyrosine-derived polycarbonates and any random or (multi-)block copolymers, such as bipolymer, terpolymer, quaterpolymer, etc., that can be polymerized from the monomers related to the previously-listed homo- and copolymers.

The fusion disc repairing material may also include additional additives that promote bone formation. Suitable bone formation promoters may include, but are not limited to, demineralized bone, all collagen types (not just type I), insoluble collagen derivatives, bone morphogenic proteins (BMPs) including BMP-2, BMP-3, BMP-4, BMP-5, BMP-6, BMP-7, BMP-8, BMP-9, BMP-10, BMP-11, BMP-12, BMP-13, BMP-14, BMP-15, BMP-16, BMP-17, and BMP-18; LIM mineralization proteins, transforming growth factor (TGF-beta), insulin-like growth factor (IGF-1) (IGF-2), platelet derived growth factor (PDGF), fibroblast growth factors (FGF), vascular endothelial growth factor (VEGF), epidermal growth factor (EGF), angiogenic agents, bone promoters, cytokines, interleukins, genetic material, genes encoding bone promoting action, cells containing genes encoding bone promoting action; hormones, growth hormones such as somatotropin; bone digestors and combinations thereof.

When treating a knee joint, the instant needle may be used to deliver visco-supplements to the joint. Because Hyaluronic Acid ("HA") is a natural component of synovial fluid and plays an essential part in its viscoelastic properties, HA is a natural candidate for a visco-supplement. Currently, there are at least five FDA approved HA based products on the market, including Euflexxa™, Hyalgan®, Synvisc®, Supartz® and Orthovisc®. Any of these products or any combinations thereof may be used as the lubricating agent for the combinations described herein. Another suitable example of the visco-supplement comprises Lubricin which is available from, for example, Affinity BioReagents, Inc. of Golden, Co.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. It should be understood that while the use of the word preferable, preferably or preferred in the description above indicates that the feature so described may be more desirable, it nonetheless may not be necessary and embodiments lacking the same may be contemplated as within the scope of the invention, that scope being defined by the claims that follow. In reading the claims it is intended that when words such as "a," "an," "at least one," "at least a portion" are used there is no intention to limit the claim to only one item unless specifically stated to the contrary in the claim. Further, when the language "at least a portion" and/or "a portion" is used the item may include a portion and/or the entire item unless specifically stated to the contrary.

What is claimed is:

1. A needle for injecting therapeutic fluid into a target space, the needle comprising:
    one or more elongated tissue-penetrating members for penetrating into a target space;
    at least one extraction orifice located on said one or more tissue-penetrating members;
    an extraction fluid path in fluid communication with said at least one extraction orifice;
    at least one injection orifice located on said one or more tissue-penetrating members and positioned remotely from said at least one extraction orifice;
    an injection fluid path in fluid communication with said at least one injection orifice;
    wherein the number of extraction and injection orifices, their size, and their position relative to each other are selected to create a pressure gradient within the target space when a therapeutic fluid is injected through the at least one injection orifice;
    a manifold having a manifold cavity wherein said one or more elongated tissue-penetrating members are attached to said manifold, said manifold cavity further comprising an internal wall configured to form a chamber within that is not in fluid communication with said manifold cavity, and a connector having a connector opening in fluid communication with said chamber and configured to allow delivery of a medical agent into said chamber without coming in fluid communication with said manifold cavity.

2. The needle of claim 1 comprising a plurality of extraction orifices and a plurality of injection orifices along one or more elongated tissue-penetrating members.

3. The needle of claim 2, wherein the size of the extraction orifices and the injection orifices is progressively varied from the distal end toward the proximal end of one or more tissue-penetrating members and the progression in size of the extraction orifices is opposite to the progression in size of injection orifices.

4. The needle of claim 3, wherein the sizes of the extraction orifices progressively increase from the distal end toward the proximal end of said one or more tissue-penetrating members, whereas the diameter of the injection orifices progressively decrease from the distal end toward the proximal end of said one or more tissue-penetrating members.

5. The needle of claim 1, wherein the target space is an intervetebral disc and the extraction orifice and the injection orifice are about 0.05 mm to about 1 mm in diameter.

6. The needle of claim 1, wherein the distance between the extraction orifice and the injection orifice is about 1 mm to about 20 mm apart.

7. The needle of claim 1, wherein the injection orifice are about 0.05 mm to about 3 mm in diameter.

8. The needle of claim 1, wherein the target space is a knee joint and the distance between the extraction orifice and the injection orifice is about 5 mm to about 20 mm.

9. The needle of claim 1 wherein the one or more extraction ports and the one or more injection ports are located relative to each other depending on the target space fluid contents being extracted and treated.

10. The needle of claim 1 wherein the one or more extraction ports enables removal of target space content at the same or faster rate than the therapeutic fluid is injected into the joint through the one or more injection ports.

11. The needle of claim 1 wherein the extraction lumen and the injection lumen are in a concentric relation to each other.

12. The needle of claim 11, wherein the outside lumen serves as an extraction lumen with at least one orifice in the sidewall and the inside lumen serves as an injection lumen with at least one orifice at the distal end.

13. The needle of claim 12, wherein the extraction lumen comprises a plurality of extraction orifices in the sidewall with progressively varied size from the distal end toward the proximal end of one or more tissue-penetrating members.

14. The needle of claim 1 wherein the extraction lumen and the injection lumen are adjacent to each other.

15. An infusion device for delivering a therapeutic fluid to a joint space comprising:

an extraction chamber having an extraction plunger slidably disposed therein;

an injection chamber fluidly isolated from the extraction chamber and having an injection plunger slidably disposed therein; and the needle of claim 1, wherein the extraction lumen of the needle is fluidly connected to the extraction chamber and the injection lumen of the needle is fluidly connected to the injection chamber.

16. The infusion device claim 15 wherein the plungers can be activated independently of each other.

17. The infusion device claim 15 wherein the plungers can be activated simultaneously of each other.

18. A method of delivering therapeutic fluid to a target space comprising the steps of:

a inserting the needle of claim 1 into the target space;

b. extracting at least a portion of the target space content from the target space; and c injecting the therapeutic fluid into the target space.

19. The method of claim 18, wherein the target space content is exchanged with the therapeutic fluid in equal amounts.

* * * * *